US010217012B2

(12) United States Patent
Hasegawa

(10) Patent No.: US 10,217,012 B2
(45) Date of Patent: Feb. 26, 2019

(54) DRUG RECOGNITION DEVICE AND METHOD

(71) Applicant: FUJIFILM Corporation, Tokyo (JP)

(72) Inventor: Kazuhide Hasegawa, Ashigarakami-gun (JP)

(73) Assignee: FUJIFILM CORPORATION, Tokyo (JP)

( * ) Notice: Subject to any disclaimer, the term of this patent is extended or adjusted under 35 U.S.C. 154(b) by 363 days.

(21) Appl. No.: 15/083,923

(22) Filed: Mar. 29, 2016

(65) Prior Publication Data

US 2016/0210524 A1    Jul. 21, 2016

Related U.S. Application Data

(63) Continuation of application No. PCT/JP2014/074815, filed on Sep. 19, 2014.

(30) Foreign Application Priority Data

Sep. 30, 2013  (JP) ................................ 2013-204899

(51) Int. Cl.
*G01N 21/95*    (2006.01)
*G06K 9/20*    (2006.01)
(Continued)

(52) U.S. Cl.
CPC .......... *G06K 9/2027* (2013.01); *G01N 21/85* (2013.01); *G01N 21/8806* (2013.01);
(Continued)

(58) Field of Classification Search
CPC .............. G06K 9/2027; G06K 9/4604; G06K 2209/01; G01N 21/9508; G01N 21/8806; G01N 21/85; G06T 2207/10152
See application file for complete search history.

(56) References Cited

U.S. PATENT DOCUMENTS

2008/0000979 A1*  1/2008  Poisner ............ G06K 19/06046
                                                      235/462.01
2013/0342676 A1* 12/2013  Amano ....................... H04N 7/18
                                                      348/86
(Continued)

FOREIGN PATENT DOCUMENTS

EP    0 172 663 A2   2/1986
JP    61-178604 A    8/1986
(Continued)

OTHER PUBLICATIONS

International Preliminary Report on Patentability, completed Aug. 10, 2015, issued in corresponding International Application No. PCT/JP2014/074815, 6 pages in English and Japanese.
(Continued)

*Primary Examiner* — Sathyanaraya V Perungavoor
*Assistant Examiner* — Howard D Brown, Jr.
(74) *Attorney, Agent, or Firm* — Sughrue Mion, PLLC

(57) ABSTRACT

An illumination unit that can illuminate a drug having a stamped character thereon in a plurality of illumination directions surrounding the drug sequentially switches the direction in which the drug is illuminated. An imaging unit repeatedly captures the image of the drug whenever the illumination direction of the illumination unit is switched. A feature image extraction unit analyzes the captured image in each illumination direction and extracts a feature image corresponding to the shadow of the stamped character from each captured image. A feature image integration unit integrates the feature images in each illumination direction which are extracted by the feature image extraction unit to generate an integrated image. The recognition unit recognizes the stamped character included in the integrated image which is generated by the feature image integration unit and
(Continued)

recognizes the type of drug on the basis of the result of recognizing the stamped character.

20 Claims, 26 Drawing Sheets

(51) Int. Cl.
    *G01N 21/85*    (2006.01)
    *G01N 21/88*    (2006.01)
    *G06K 9/46*    (2006.01)

(52) U.S. Cl.
    CPC ....... *G01N 21/9508* (2013.01); *G06K 9/4604* (2013.01); *G06K 2209/01* (2013.01); *G06T 2207/10152* (2013.01)

(56) References Cited

U.S. PATENT DOCUMENTS

| | | | | |
|---|---|---|---|---|
| 2015/0170373 A1* | 6/2015 | Yonaha | ............... | G06K 9/00 382/143 |
| 2015/0178674 A1* | 6/2015 | Yonaha | ............... | G06Q 50/22 705/2 |
| 2016/0077091 A1* | 3/2016 | Tyrrell | ............. | G01N 33/48792 436/501 |
| 2016/0104282 A1* | 4/2016 | Takahashi | ............... | B65B 37/04 382/103 |
| 2016/0109385 A1* | 4/2016 | Tanimoto | ........... | G01N 21/8851 356/432 |

FOREIGN PATENT DOCUMENTS

| | | |
|---|---|---|
| JP | 61-228305 A | 10/1986 |
| JP | 9-297107 A | 11/1997 |
| JP | 10-185832 A | 7/1998 |
| JP | 2010-117331 A | 5/2010 |
| JP | 2010-190786 A | 9/2010 |
| JP | 2011-137675 A | 7/2011 |
| JP | 2012-165876 A | 9/2012 |
| JP | 2013-148454 A | 8/2013 |

OTHER PUBLICATIONS

International Search Report of PCT/JP2014/074815, dated Nov. 18, 2014. [PCT/ISA/210].

Written Opinion of PCT/JP2014/074815, dated Nov. 18, 2014. [PCT/ISA/237].

Notification of Reasons for Refusal, dated Nov. 10, 2016, issued in corresponding JP Application No. 2013-204899, 6 pages in English and Japanese.

* cited by examiner

FIG. 10
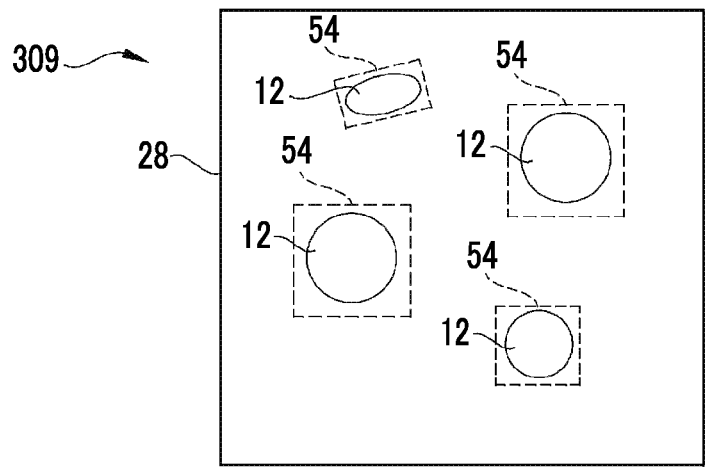
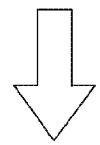
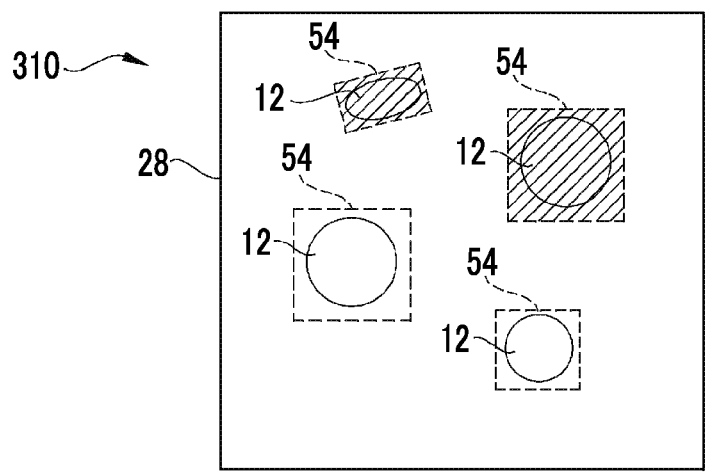

DRUG RECOGNITION DEVICE AND METHOD

CROSS-REFERENCE TO RELATED APPLICATIONS

The present application is a Continuation of PCT International Application No. PCT/JP2014/074815 filed on Sep. 19, 2014 claiming priority under 35 U.S.C § 119(a) to Japanese Patent Application No. 2013-204899 filed on Sep. 30, 2013. Each of the above applications is hereby expressly incorporated by reference, in their entirety, into the present application.

BACKGROUND OF THE INVENTION

1. Field of the Invention

The present invention relates to a drug recognition device and a drug recognition method which recognize the type of drug having a stamped character thereon.

2. Description of the Related Art

In recent years, for example, when a doctor prescribes a plurality of types of drug which are taken at different times (for example, after breakfast, after lunch, and after dinner) for a patient in hospitals, unit-dose packaging which dispenses and packages a plurality of types of drug (for example, tablets or capsules) corresponding to one dose in one packet has been generally performed. Unit-dose packaging means that drugs corresponding to each dose which are picked by the pharmacist according to a prescription are set in a tray (also referred to as a tablet case) of a packaging machine and the packaging machine automatically packages the drugs in the tray in each packet. In the unit-dose packaging, in some cases, the pharmacist manually performs the picking of the drugs or the setting of the drugs in the tray. Therefore, the type of drug or the number of drugs which is different from that written in the prescription is likely to be erroneously packaged in a packet. For this reason, in order to determine whether the drugs packaged in a packet match those written in the prescription, the type of drug or the number of drugs is automatically recognized before or after the drugs are packaged in the packet.

For example, JP2012-165876A discloses an inspection device which captures the image of each packet of drugs set on a transparent plate, using cameras that are provided in a direction perpendicular to the transparent plate, and performs imaging processing for the captured images obtained by each camera to automatically recognize characters printed or stamped on the drugs. It is possible to recognize the type of drug on the basis of the result of recognizing the characters printed or stamped on the drug.

JP2013-148454A discloses a tablet inspection device which irradiates drugs packaged in a packet with parallel light and diffuse light at different times, captures the image of the drugs illuminated with each light component, generates a difference image between the image captured when the parallel light is emitted and the image captured when the diffuse light is emitted, and counts the number of drugs on the basis of the difference image.

JP2010-190786A discloses a print inspection device which illuminates a drug while switching the set amount (illumination conditions) of light from an illumination unit, captures the image of the drug whenever the illumination conditions are switched, and performs image processing (binarization process) for the image captured under each illumination condition to extract characters printed on the drug. Then, the print inspection device determines the optimum illumination condition in which the contrast between the printed characters and the background is the maximum among the illumination conditions and performs a process of capturing the image of the drug and image processing under the optimum illumination condition to recognize the characters (type name) printed on the drug.

JP2010-117331A discloses a granular article type inspection device which illuminates a drug in one illumination direction, using an illumination unit that can illuminate the drug in a plurality of illumination directions, captures the image of the drug to acquire a captured image, and performs image processing for the captured image to extract characters printed or stamped on the drug. Then, in a case in which the extraction of the printed characters or the stamped characters from the captured image has failed, the granular article type inspection device switches the illumination direction of the illumination unit, performs the imaging process and image processing again, and recognizes the characters printed or stamped on the drug.

SUMMARY OF THE INVENTION

However, each of the devices disclosed in JP2012-165876A, JP2013-148454A, JP2010-190786A, and JP2010-117331A performs image processing for the captured image of the drugs to recognize the characters printed or stamped on the drugs or the number of drugs. However, the illumination conditions suitable for recognizing the printed characters, the stamped characters, and the number of drugs are different from each other. In particular, since the stamped characters are formed by grooves provided in the surface of the drugs, the device receives illumination light and recognizes the shadow generated by a groove portion of the stamped character as a character during the recognition of the stamped characters. However, the size and direction of the shadow, and whether or not the shadow is generated vary depending on the illumination direction. In addition, when the incident angle (the height of illumination) of illumination light as one of the illumination directions varies, the intensity of the shadow varies.

For example, each drug is set on an inspection tray during imaging. It is difficult to change the direction or position of the drug on the inspection tray during imaging. Therefore, the direction in which a shadow is generated, whether or not a shadow is generated, and the intensity of a shadow vary depending on the illumination direction or the surface shape of the drug (a planar shape or a curved shape). For this reason, it is difficult for each of the devices disclosed in JP2012-165876A, JP2013-148454A, JP2010-190786A, and JP2010-117331A to accurately recognize the stamped characters. As a result, it is difficult to accurately recognize the type of drug having characters stamped thereon.

An object of the invention is to provide a drug recognition device and a drug recognition method which can accurately recognize the type of drug having characters stamped thereon.

In order to achieve the object, according to an aspect of the invention, there is provided a drug recognition device including: an illumination unit that can illuminate a drug having a stamped character thereon in a plurality of illumination directions surrounding the drug; an illumination control unit that sequentially switches the illumination direction in which the illumination unit illuminates the drug; an imaging unit that captures an image of the drug illuminated by the illumination unit and repeatedly captures the image of the drug whenever the illumination direction is switched; a feature image extraction unit that extracts a feature image corresponding to a shadow of the stamped character from the captured image in each illumination direction which is acquired by the imaging unit; a feature image integration unit that integrates the feature images in each illumination direction which are extracted by the feature image extraction unit to generate an integrated image; and a recognition unit that recognizes the stamped character included in the integrated image which is generated by the feature image integration unit and recognizes the type of the drug on the basis of the result of recognizing the stamped character.

In the drug recognition device according to the above-mentioned aspect of the invention, it is possible to accurately recognize the stamped character on the drug, without being affected by the illumination direction in which the drug is illuminated or the surface shape of the drug.

It is preferable that the drug recognition device further includes a drug position detection unit that detects the position of the image of the drug included in the captured image. It is preferable that the illumination unit changes the amount of illumination light for illuminating the drug in each illumination direction. It is preferable that the illumination control unit calculates a positional relationship between the drug and a light source in each illumination direction of the illumination unit, on the basis of the detection result of the drug position detection unit, and controls the illumination unit on the basis of the calculation result of the positional relationship such that a uniform amount of illumination light is incident on the drug in each illumination direction. According to this structure, a uniform amount of illumination light can be incident on the drug in each illumination direction. Therefore, it is possible to uniformize the brightness distribution of the drug in the captured image. As a result, the probability of success in recognizing the stamped character increases.

It is preferable that the illumination unit changes the amount of illumination light for illuminating the drug in each illumination direction. It is preferable that the imaging unit captures the image of the drug which is illuminated in all of the illumination directions at the same time by the illumination unit and acquires a previously captured image. It is preferable that the drug recognition device further includes a brightness distribution analysis unit that analyzes a brightness distribution of the image of the drug included in the previously captured image. It is preferable that the illumination control unit controls the illumination unit on the basis of the analysis result of the brightness distribution analysis unit such that a uniform amount of illumination light is incident on the drug in each illumination direction. According to this structure, a uniform amount of illumination light can be incident on the drug in each illumination direction. Therefore, it is possible to uniformize the brightness distribution of the drug in the captured image. As a result, the probability of success in recognizing the stamped character increases.

It is preferable that the illumination unit switches sub-illumination conditions of the illumination unit which are different from the switching of the illumination direction. It is preferable that the illumination control unit controls the illumination unit such that the illumination direction is switched under each sub-illumination condition, while switching the sub-illumination conditions. Since the sub-illumination conditions are switched, it is possible to capture the image of the drug under the illumination conditions suitable for recognizing the stamped character. Therefore, it is possible to accurately recognize the stamped character (that is, the type of drug).

In a case in which an image of a plurality of drugs is included in the captured image, it is preferable that the illumination control unit controls the illumination unit such that the sub-illumination conditions are repeatedly switched until the recognition unit succeeds in recognizing the types of all of the drugs. According to this structure, it is possible to capture the image of the drug under the illumination conditions suitable for recognizing the stamped character.

It is preferable that the feature image extraction unit stops the extraction of the feature image from a region corresponding to the drug, of which the type has been successfully recognized by the recognition unit, in the captured image. According to this structure, it is possible to reduce the time required to recognize the drug and to reduce the load of a calculation process.

It is preferable that the drug recognition device further includes a dispensing information acquisition unit that acquires dispensing information. It is preferable that the illumination unit illuminates each packet of drugs which are packaged in a plurality of packets according to the dispensing information. It is preferable that the recognition unit discriminates the stamped character on the drug which is recorded in the dispensing information acquired by the dispensing information acquisition unit, compares the result of discriminating the stamped character with the integrated image to recognize the stamped character included in the integrated image, and recognizes the types of the drugs corresponding to one packet on the basis of the result of recognizing the stamped character. According to this structure, it is possible to reduce errors in the recognition of the stamped character.

It is preferable that the drug recognition device further includes: an inspection unit that collates the result of recognizing the types of the drugs corresponding to one packet obtained by the recognition unit with the types of drug corresponding to one packet which are recorded in the dispensing information; and a display unit that displays the collation result of the inspection unit. According to this structure, it is possible to inform a user, such as a pharmacist, of the collation result.

It is preferable that the feature image extraction unit extracts the feature image from the captured image using an edge detection process. According to this structure, it is possible to accurately extract the feature image.

It is preferable that the illumination unit includes a plurality of point light sources that are provided around the drugs. It is preferable that the illumination control unit turns each of the point light sources on and off to switch the illumination direction. According to this structure, it is possible to irradiate the drug with illumination light in a plurality of illumination directions surrounding the drug.

It is preferable that the drug recognition device further includes a drug movement mechanism that moves the drug and the illumination unit between a first position and a second position in a horizontal direction. It is preferable that the imaging unit includes a first imaging unit that captures an image of one surface of the drug in a case in which the drug is at the first position and a second imaging unit that captures an image of the other surface opposite to the one surface of the drug in a case in which the drug is at the second position. It is preferable that the feature image extraction unit extracts the feature images from the captured images in each illumination direction which are acquired by the first imaging unit and the second imaging unit. It is preferable that the feature image integration unit integrates the feature images in each illumination direction which correspond to the one surface and integrates the feature images in each illumination direction which correspond to the other surface to generate the integrated images corresponding to the one surface and the other surface. It is preferable that the recognition unit recognizes the stamped character on at least one of the one surface and the other surface of the drug, on the basis of the integrated images corresponding to the one surface and the other surface, and recognizes the type of the drug. According to this structure, even in a case in which the character is stamped on only one of both surfaces of the drug, it is possible to recognize the stamped character and thus to recognize the type of drug.

In order to achieve the object of the invention, according to another aspect of the invention, there is provided a drug recognition method including: an illumination control step of sequentially switching a plurality of illumination directions which surround a drug having a stamped character thereon and in which an illumination unit can illuminate the drug; an imaging step of repeatedly capturing an image of the drug illuminated by the illumination unit whenever the illumination direction is switched in the illumination control step; a feature image extraction step of extracting a feature image corresponding to a shadow of the stamped character from the captured image in each illumination direction which is acquired in the imaging step; a feature image integration step of integrating the feature images in each illumination direction which are extracted in the feature image extraction step to generate an integrated image; and a recognition step of recognizing the stamped character on the basis of the integrated image generated in the feature image integration step and recognizing the type of the drug on the basis of the result of recognizing the stamped character.

According to the drug recognition device and the drug recognition method of the invention, it is possible to accurately recognize the type of drug having a stamped character thereon.

BRIEF DESCRIPTION OF THE DRAWINGS

FIG. 10 is a diagram illustrating a masking process of a masking unit.

DESCRIPTION OF THE PREFERRED EMBODIMENTS

[Overall Structure of Drug Inspection Device According to First Embodiment]

Figure 1:
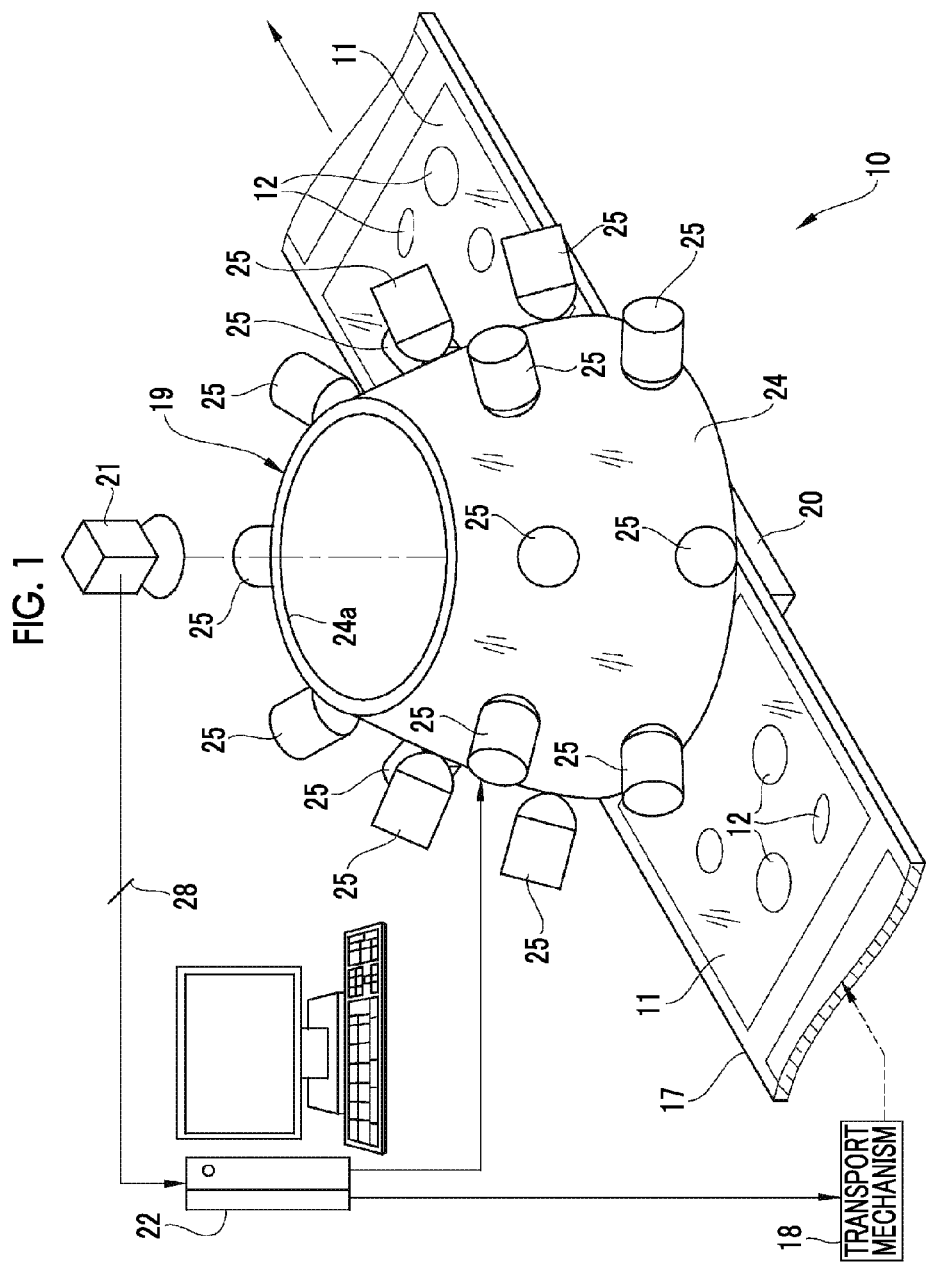
FIG. 1 is a perspective view illustrating a drug inspection device according to a first embodiment.
Figure 2:
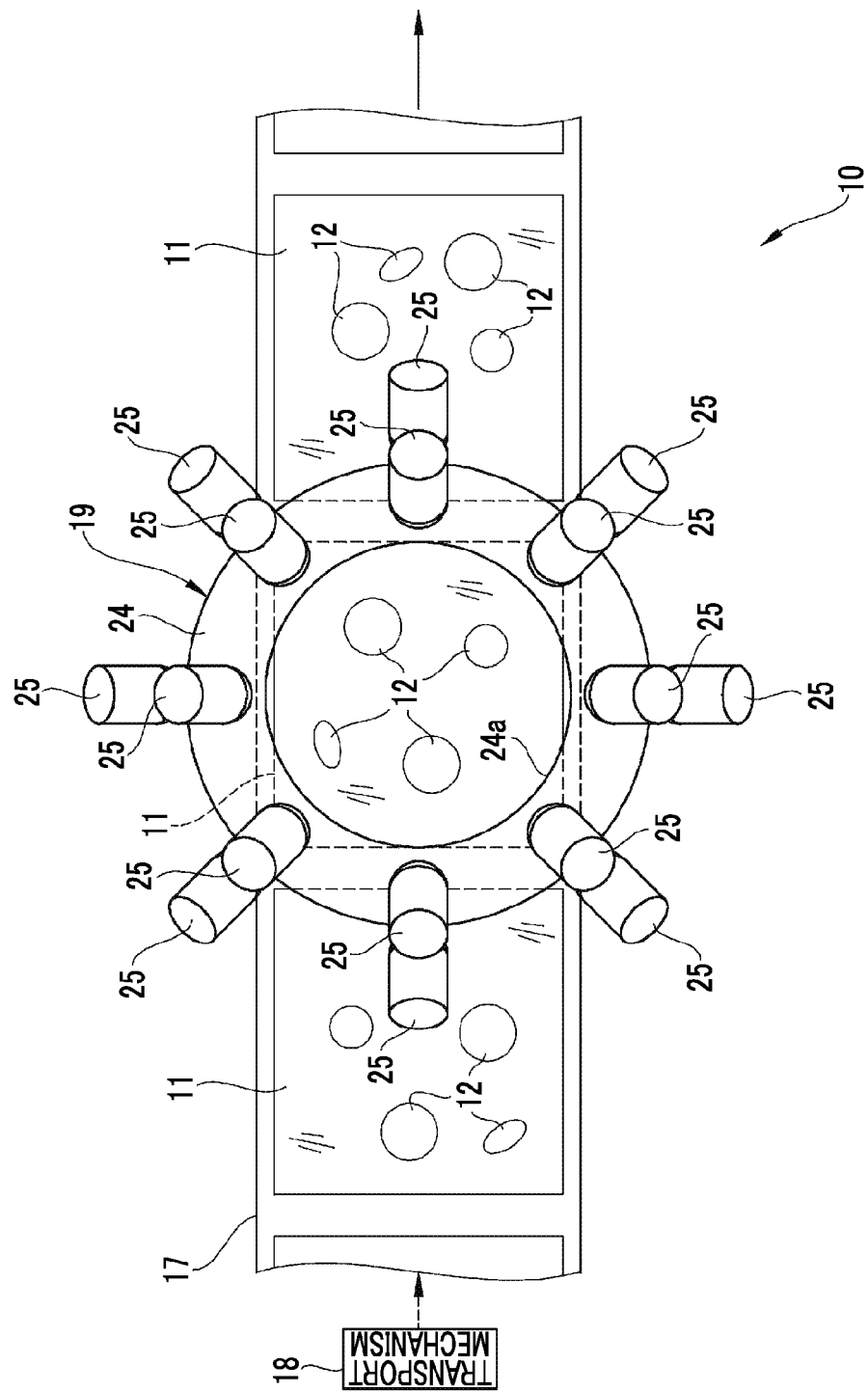
FIG. 2 is a top view illustrating a floodlight of the drug inspection device illustrated in FIG. 1.

As illustrated in FIGS. 1 and 2, a drug inspection device (drug recognition device) 10 recognizes the type of drug 12 packaged in a transparent (including semitransparent, which holds for the following description) packet 11 and checks whether the drugs 12 in the packet 11 are dispensed according to a prescription (not illustrated). Here, the drug 12 is a solid drug having a stamped character 14 (see FIG. 5) on the surface thereof and is, for example, a tablet or a capsule. The stamped character 14 is a character or a symbol which is formed by a groove provided in the surface of the drug 12 and indicates the type (product number) of drug 12.

The drug inspection device 10 mainly includes a tray 17, a transport mechanism 18, a floodlight (illumination unit) 19, a backlight 20, a camera 21, and a device body 22.

A series of packets 11, each of which has the drugs 12 corresponding to one packet and is packaged by a packaging device (not illustrated), is placed on the tray 17. The tray 17 is made of a transparent material so as to transmit illumination light emitted from the backlight 20 which will be described below.

The transport mechanism 18 intermittently transports the tray 17 along the longitudinal direction of a series of packets 11 (hereinafter, simply referred to as a longitudinal direction). Therefore, it is possible to transport a series of packets 11 in the longitudinal direction relative to the floodlight 19, which will be described below, the backlight 20, and the camera 21. In addition, the floodlight 19, the backlight 20, and the camera 21 may be transported in the longitudinal direction, instead of transporting the tray 17.

The floodlight 19 is provided on the upper surface side of the tray 17 in FIG. 1 and sequentially illuminates each packet in the series of packets 11 which are intermittently transported in the longitudinal direction by the transport mechanism 18. The floodlight 19 includes a transparent light source holding unit 24 and a plurality of point light sources 25 which are attached to the light source holding unit 24.

The light source holding unit 24 has a substantially domic shape which covers one packet 11. An opening window 24a through which the inside of the light source holding unit 24 is exposed is formed at the top of the light source holding unit 24. Therefore, it is possible to check the drugs 12 (hereinafter, simply referred to as the drugs 12 in the light source holding unit 24) which are packaged in the packet 11 in the light source holding unit 24 through the opening window 24a from the upper side of the light source holding unit 24.

For example, an LED light source is used as the point light source 25. Eight point light sources 25 are attached to a lower end portion of the outside surface of the light source holding unit 24 (hereinafter, referred to as a lower end portion of the outside surface) at equal intervals in the circumferential direction and eight point light sources 25 are attached to an upper end portion of the outside surface of the light source holding unit 24 (hereinafter, referred to as an upper end portion of the outside surface) at equal intervals in the circumferential direction. That is, each point light source 25 is arranged so as to surround the drugs 12 in the light source holding unit 24. The 16 point light sources 25 emit illumination light to the drugs 12 in the light source holding unit 24. The illumination light which is emitted from the eight point light sources 25 attached to the lower end portion of the outside surface is incident on the drugs 12 in the light source holding unit 24 at a low incident angle (low angle). In contrast, the illumination light which is emitted from the eight point light sources 25 attached to the upper end portion of the outside surface is incident on the drugs 12 in the light source holding unit 24 at a high incident angle (high angle).

The floodlight 19 can illuminate the drugs 12 in the light source holding unit 24 in a plurality of illumination directions, using each point light source 25. In addition, the floodlight 19 can control the turn-on and turn-off (switching) of each of the 16 point light sources to switch the illumination direction in which the drugs 12 in the light source holding unit 24 are illuminated (hereinafter, simply referred to as an illumination direction).

For example, the floodlight 19 can sequentially turn on and off the 16 point light sources to switch the illumination direction 16 times, that is, to sequentially switch the illumination direction to 16 directions. In addition, in the floodlight 19, two point light sources 25 which are attached to the lower end portion and the upper end portion of the outside surface in the circumferential direction, that is, at the same position on the outside surface in the circumferential direction form a set and sets of the point light sources 25 are sequentially turned on and off in the circumferential direction of the outside surface to switch the illumination direction eight times, that is, to sequentially switch the illumination direction to eight directions. Furthermore, in the floodlight 19, every other set of the point light sources 25 can be sequentially turned on and off in the circumferential direction of the outside surface to switch the illumination direction four times, that is, to sequentially switch the illumination direction to four directions.

The backlight 20 is provided on the lower surface side of the tray 17 in FIG. 1 and is arranged below the floodlight 19. The backlight 20 illuminates the drugs 12 in the light source holding unit 24 from the rear side through the transparent tray 17.

The camera 21 is provided above the opening window 24a. The camera 21 captures the image of the drugs 12 in the light source holding unit 24 through the opening windows 24a and generates captured image data 28. The camera 21 outputs the captured image data 28 to the device body 22.

<Structure of Device Body According to First Embodiment>

The device body 22 is connected to the transport mechanism 18, the floodlight 19, the backlight 20, and the camera 21 (connection to the backlight 20 is not illustrated). The device body 22 controls the operation of the transport mechanism 18, the floodlight 19, the backlight 20, and the camera 21.

Figure 3:
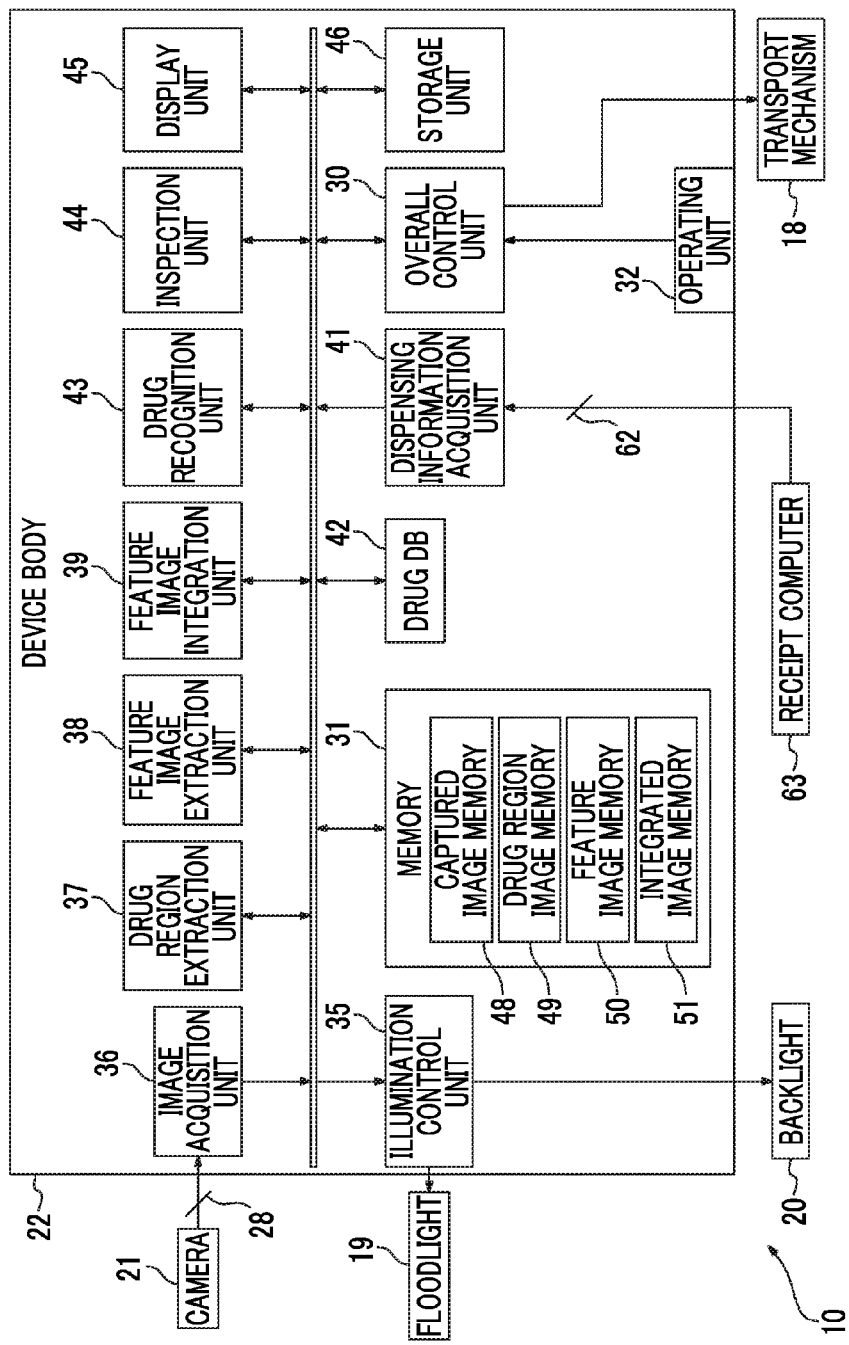
FIG. 3 is a block diagram illustrating the electrical structure of the drug inspection device according to the first embodiment.

As illustrated in FIG. 3, the device body 22 includes, for example, an overall control unit 30, a memory 31, an operating unit 32, an illumination control unit 35, an image acquisition unit 36, a drug region extraction unit 37, a feature image extraction unit 38, a feature image integration unit 39, a dispensing information acquisition unit 41, a drug database (hereinafter, simply referred to as a drug DB) 42, a drug recognition unit (recognition unit) 43, an inspection unit 44, a display unit 45, and a storage unit 46.

The overall control unit 30 reads various kinds of control programs or data stored in the memory 31 and executes the read programs or data to perform overall control for each unit of the device body 22, in response to an operation instruction which is input to the operating unit 32. The memory 31 includes a captured image memory 48, a drug region image memory 49, a feature image memory 50, and an integrated image memory 51 that store various kinds of image data (which will be described below) acquired or generated by each unit of the device body 22, in addition to the above-mentioned programs or data.

The illumination control unit 35 controls the emission of illumination light by the floodlight 19 and the backlight 20 under the control of the overall control unit 30. In addition, the illumination control unit 35 switches the illumination conditions in which the floodlight 19 illuminates the drugs 12 in the light source holding unit 24. In the first embodiment, it is assumed that only the switching of the illumination direction is performed as the switching of the illumination conditions and the number of times the illumination direction is switched is set to 4 (any value other than 4 is possible). The "switching of the illumination directions" means the rotation (see FIG. 6) of the direction in which the drugs 12 are illuminated. In addition, it is assumed that the backlight 20 is maintained in an on state or an off state. The illumination control unit 35 controls the floodlight 19 such that the sets of the point light sources 25 are sequentially turned on and off in the circumferential direction of the outside surface of the light source holding unit 24. Therefore, it is possible to sequentially switch the illumination direction to four directions.

The image acquisition unit 36 controls the capture of images by the camera 21 under the control of the overall control unit 30 and acquires the captured image data 28 from the camera 21. Whenever the illumination control unit 35 switches the illumination conditions, that is, whenever the illumination direction of the floodlight 19 is switched, the image acquisition unit 36 directs the camera 21 to capture an image and acquires the captured image data 28 from the camera 21. In this way, the captured image data 28 (hereinafter, referred to as four-direction captured image data 28) obtained by capturing the image of the drugs 12 in the light source holding unit 24 in four directions is sequentially obtained. Then, the image acquisition unit 36 sequentially stores the four-direction captured image data 28 acquired from the camera 21 in the captured image memory 48.

Figure 4:
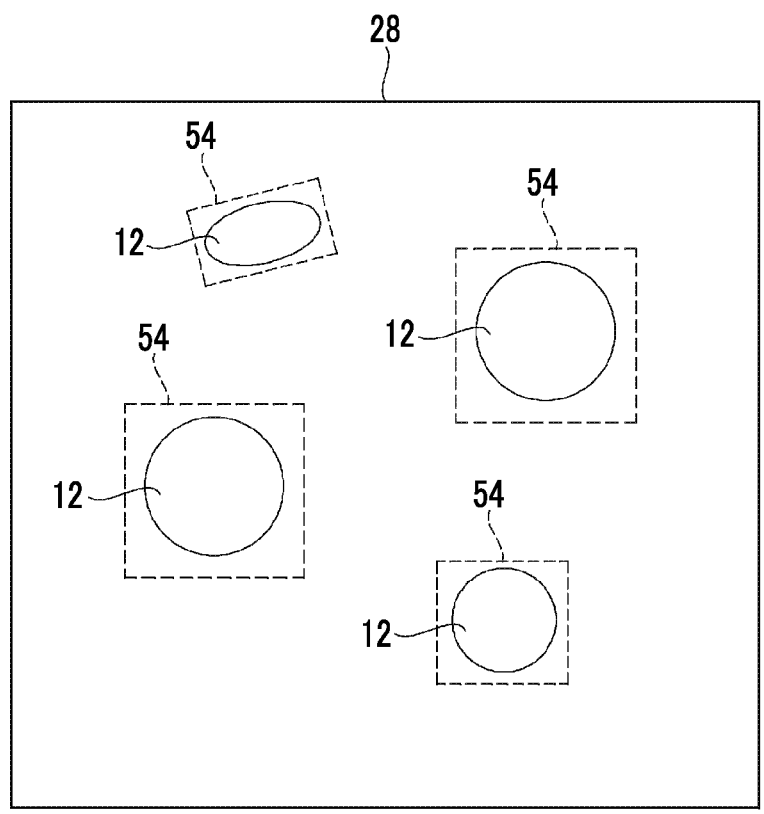
FIG. 4 is a diagram illustrating a process of extracting drug region image data.

As illustrated in FIG. 4, whenever the illumination direction is switched, the drug region extraction unit 37 sequentially reads the four-direction captured image data 28 from the captured image memory 48 and extracts drug region image data 54 corresponding to a region of the drug 12 from the four-direction captured image data 28. For example, the drug region extraction unit 37 extracts the contour of the drug 12 in the image, using a known edge detection process or a known segmentation process, and extracts the drug region image data 54 in four directions from the four-direction captured image data 28.

Here, in the four-direction captured image data 28, the drug region image data 54 corresponding to the same drug 12 is located at the same position. Therefore, the drug region image data 54 (hereinafter, referred to as four-direction drug region image data 54) for each of the drugs 12 corresponding to one packet in four illumination directions is obtained from the four-direction captured image data 28. Then, the drug region extraction unit 37 sequentially stores the four-direction drug region image data 54 for each drug 12 in the drug region image memory 49.

Returning to FIG. 3, whenever the illumination direction is switched, the feature image extraction unit 38 sequentially reads the four-direction drug region image data 54 for each drug 12 from the drug region image memory 49, analyzes the four-direction drug region image data 54, and extracts an image corresponding to the shadow of each stamped character 14 from each drug region image data item 54.

Figure 5:
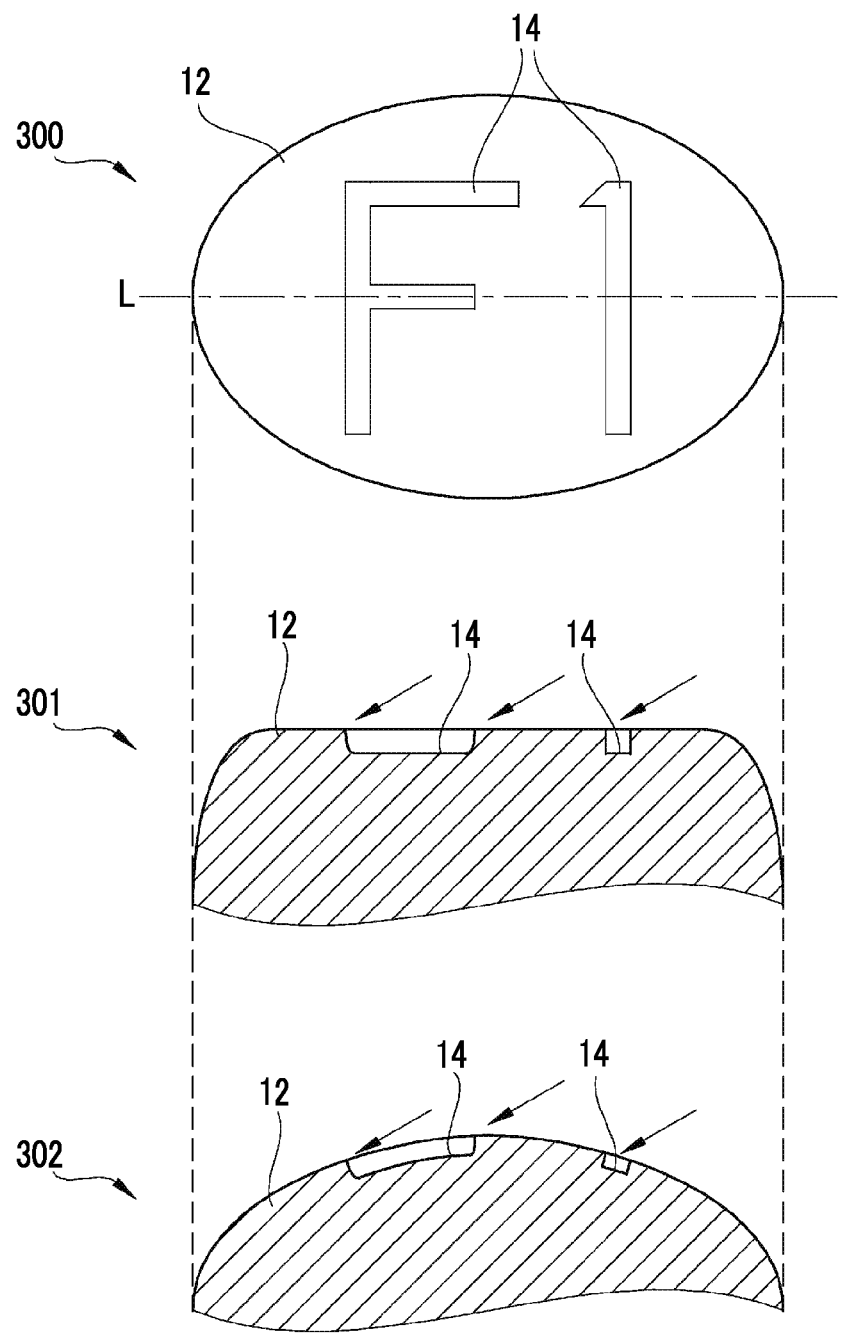
FIG. 5 is a plan view and a cross-sectional view illustrating a drug having stamped characters thereon.

As illustrated in FIG. 5, the stamped character 14 is formed by a groove which is provided in the surface of the drug 12. In FIG. 5, reference numeral 300 indicates the front view of the stamped character, reference numeral 301 indicates the cross-sectional view of the drug 12 taken along a straight line L in FIG. 5, and reference numeral 302 indicates the cross-sectional view of the drug 12 which has a different surface shape from that in the cross-sectional view indicated by reference numeral 301. When the stamped character 14 is illuminated in one direction, a shadow is generated according to the contour of the stamped character 14 on the illumination light source side. The direction, shape, and intensity of the shadow vary depending on the illumination direction, the shape of the stamped character 14, and the surface shape of the drug 12.

Figure 6:
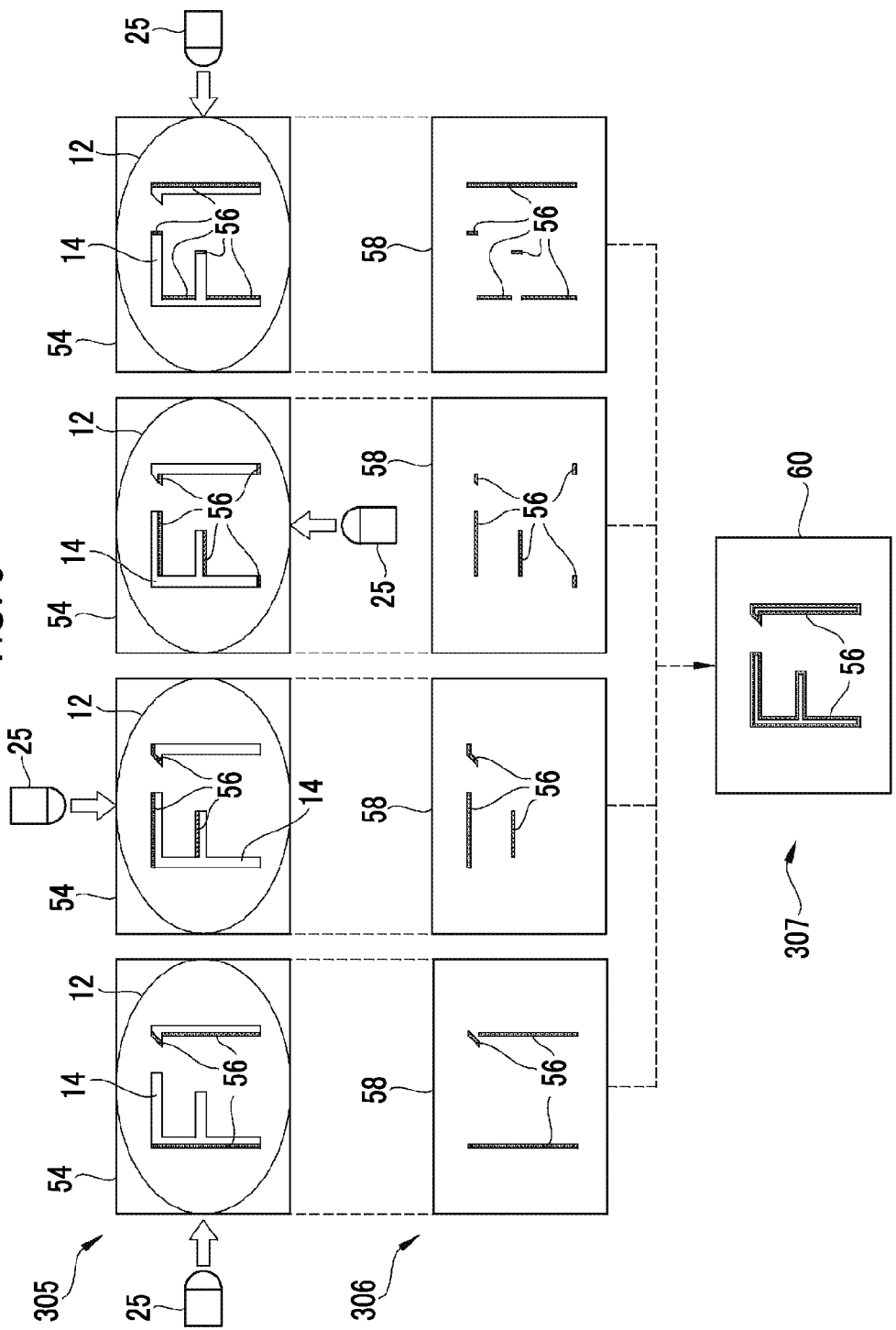
FIG. 6 is a diagram illustrating a process of extracting feature image data and a process of generating integrated image data.

As illustrated on the upper side (reference numeral 305) of FIG. 6, in the four-direction drug region image data 54, a shadow image 56 is generated according to the contour of the stamped character 14 on the illumination light source side (on the side of the point light source 25 which emits illumination light). In addition, since the stamped character 14 has the same color as the surface of the drug 12, it is difficult to discriminate the stamped character 14 in the actual image. However, in the drawings, the stamped character 14 is illustrated so as to be discriminated in order to describe the relationship between the stamped character 14 and the shadow image 56 corresponding to the illumination direction.

As illustrated in the middle (reference numeral 306) of FIG. 6, the feature image extraction unit 38 performs an edge detection process on the four-direction drug region image data 54 for each drug 12 to extract feature image data 58 corresponding to the shadow image 56 from each drug region image data item 54. Therefore, the feature image data 58 for each of the drugs 12 corresponding to one packet in four illumination directions (hereinafter, referred to as four-direction feature image data 58) is obtained. Then, the feature image extraction unit 38 sequentially stores the four-direction feature image data 58 for each drug 12 in the feature image memory 50 (see FIG. 3).

As illustrated in the lower portion (reference numeral 307) of FIG. 6, the feature image integration unit 39 reads the four-direction feature image data 58 for each of the drugs 12 corresponding to one packet from the feature image memory 50 and integrates the four-direction feature image data 58 for each drug 12 to generate integrated image data 60. For example, the feature image integration unit 39 overlaps the four-direction feature image data 58 to integrate the four-direction feature image data 58. Then, since the shadow images 56 in four illumination directions are integrated into one image, the entire stamped character 14 is outlined in the integrated image data 60. Then, the feature image integration unit 39 generates the integrated image data 60 for each of the drugs 12 corresponding to one packet and stores each integrated image data item 60 in the integrated image memory 51 (see FIG. 3).

Returning to FIG. 3, the dispensing information acquisition unit 41 acquires dispensing information 62 which is written in a prescription for the drugs 12 packaged in a series of packets 11 on the tray 17 from a receipt computer 63 (a computer which manages information such as a medical fee). A pharmacist inputs the dispensing information 62 written in the prescription to the receipt computer 63 in advance. The above-mentioned packaging device packages the drugs 12 in a series of packets 11 according to the dispensing information 62 input to the receipt computer 63. It is possible to discriminate the drugs 12 to be packaged in the packet 11 in the light source holding unit 24, that is, the type of drug 12 or the number of drugs 12 which are currently illuminated by the floodlight 19, on the basis of the dispensing information 62 acquired by the dispensing information acquisition unit 41.

For example, the appearance image of the drug 12 or the image of the stamped character 14 is registered in the drug DB 42 so as to be associated with the type of drug 12. Therefore, it is possible to discriminate the stamped character 14 on the drug 12 from the type of drug 12, with reference to the drug DB 42. In addition, inversely, it is possible to discriminate the type of drug 12 from the stamped character 14.

The drug recognition unit 43 reads the integrated image data 60 for the drugs 12 corresponding to one packet from the integrated image memory 51 and recognizes the type of each drug 12 on the basis of each integrated image data item 60. First, the drug recognition unit 43 discriminates the stamped character 14 on each of the drugs 12 which are recorded in the dispensing information 62 on the basis of the dispensing information 62 acquired by the dispensing information acquisition unit 41, with reference to the drug DB 42. Each drug 12 recorded in the dispensing information 62 is, for example, all types of drugs 12 which are set in the packaging device or the drugs 12 corresponding to one packet which are currently set in the light source holding unit 24.

Then, the drug recognition unit 43 compares the discrimination result of the stamped character 14 based on the dispensing information 62 with each integrated image data item 60 (for example, a matching process) to recognize each stamped character 14 included in each integrated image data item 60. Then, the drug recognition unit 43 recognizes the type of drug 12 corresponding to each stamped character 14 on the basis of the result of recognizing the stamped character 14 in each integrated image data item 60, with reference to the drug DB 42. In this way, the types of drug 12 corresponding to one packet are recognized. Then, the drug recognition unit 43 outputs the result of recognizing the types of drug 12 corresponding to one packet to the inspection unit 44.

In addition, in a case in which the stamped character 14 included in the integrated image data 60 is too unclear to be recognized, the drug recognition unit 43 determines that the recognition of the drug 12 corresponding to the integrated image data 60 has failed and outputs the determination result to the display unit 45.

The inspection unit 44 collates the result of recognizing the types of drugs 12 corresponding to one packet which is input from the drug recognition unit 43 with the types of drugs 12 corresponding to one packet which are recorded in the dispensing information 62 acquired by the dispensing information acquisition unit 41. Then, the inspection unit 44 outputs the collation result to the display unit 45 and the storage unit 46.

The display unit 45 displays the collation result input from the inspection unit 44. In a case in which the collation result shows the mismatch therebetween, the display unit 45 displays the type name of the corresponding drug 12 (the drug 12 which is erroneously packaged in the packet 11). In a case in which the determination result indicating that the recognition of the drug 12 has failed is received from the drug recognition unit 43, the display unit 45 displays the determination result. In addition, the display unit 45 may perform, for example, a process of outputting a voice from a speaker, in addition to the process of displaying the collation result on a display screen.

The storage unit 46 stores the collation result input from the inspection unit 44. In addition, the storage unit 46 may read the four-direction captured image data 28 corresponding to the collation result from the captured image memory 48 and store the four-direction captured image data 28, in addition to the collation result.

The overall control unit 30 controls each unit of the device body 22 to repeatedly perform the intermittent transport of a series of packets 11 and the recognition and inspection of the drugs 12 corresponding to one packet set in the light source holding unit 24.

[Operation of Drug Inspection Device According to First Embodiment]

Figure 7:
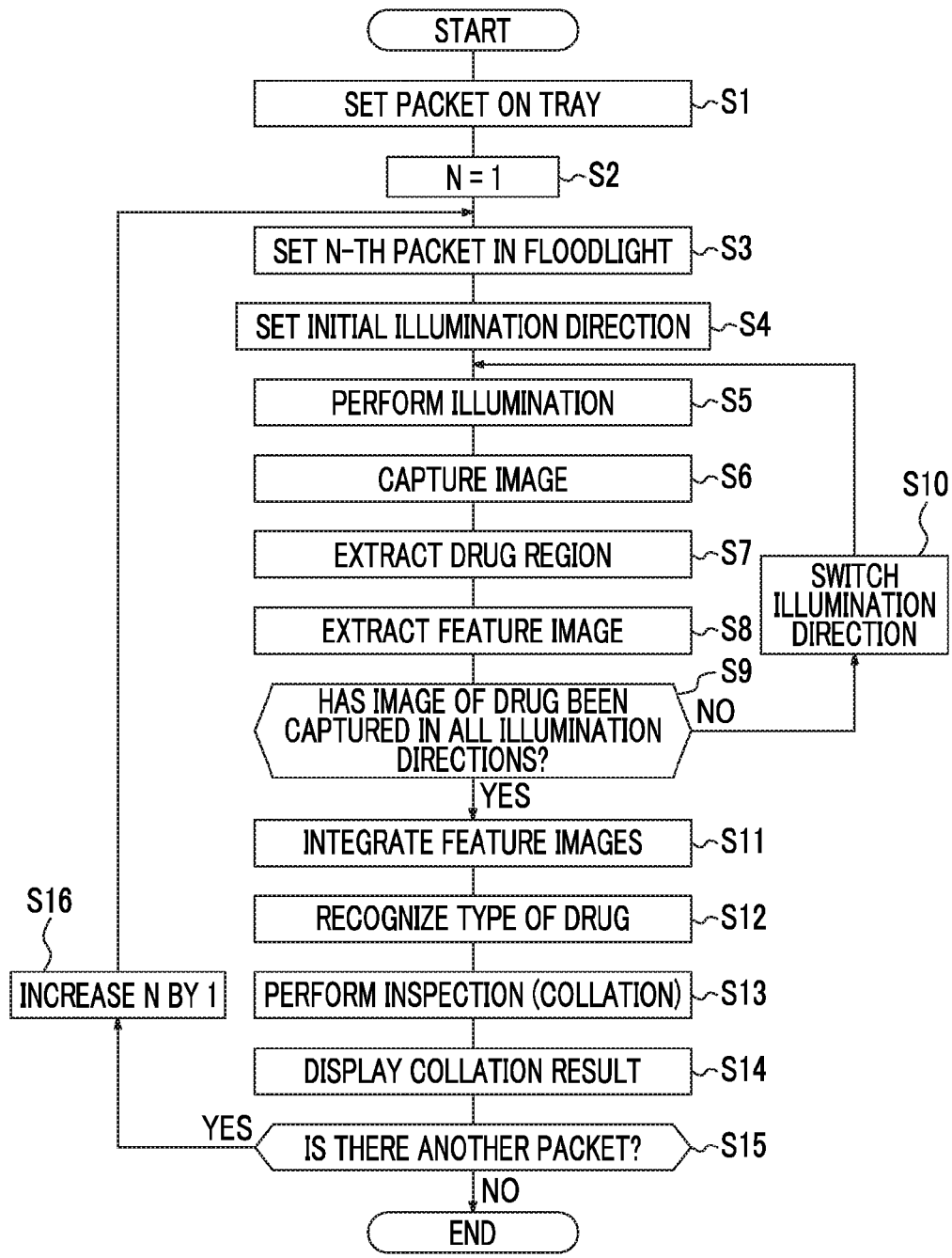
FIG. 7 is a flowchart illustrating the flow of an inspection process of the drug inspection device according to the first embodiment.

Next, the operation of the drug inspection device 10 having the above-mentioned structure will be described with reference to FIG. 7. The pharmacist sets the drugs 12 in the packaging device according to the dispensing information 62 which is input to the receipt computer 63 in advance. Then, the packaging device packages the drugs 12 in a plurality of packets 11. The series of packets 11 having the drugs 12 packaged by the packaging device is set on the tray 17 of the drug inspection device 10 (Step S1). Then, when an inspection start operation is performed through the operating unit 32, the overall control unit 30 operates each unit of the device body 22 to start the recognition and inspection of the types of drug 12 packaged in the series of packet 11.

First, the transport mechanism 18 transports the tray 17 in the longitudinal direction to set a first (N=1: Step S2) packet 11 in the light source holding unit 24 (Step S3). Then, the illumination control unit 35 sets any one of four illumination directions to an initial illumination direction (Step S4) and controls the floodlight 19 such that a set of the point light sources 25 corresponding to the initial illumination direction is turned on. Then, the drug 12 in the light source holding unit 24 is illuminated in the initial illumination direction by the set of the point light sources 25 (Step S5).

When the illumination of the drug 12 in the initial illumination direction starts, the image acquisition unit 36 directs the camera 21 to capture the image of the drug, acquires the captured image data 28 from the camera 21, and stores the captured image data 28 in the captured image memory 48 (Step S6, an imaging step).

When the captured image data 28 in the initial illumination direction is newly stored in the captured image memory 48, the drug region extraction unit 37 reads the captured image data 28 in the initial illumination direction from the captured image memory 48. Then, the drug region extraction unit 37 extracts the drug region image data 54 for each drug 12 from the captured image data 28 in the initial illumination direction and stores the drug region image data 54 in the drug region image memory 49 (Step S7). In this way, the drug region image data 54 for each drug 12 in the initial illumination direction is stored in the drug region image memory 49.

When the drug region image data 54 for each drug 12 in the initial illumination direction is newly stored in the drug region image memory 49, the feature image extraction unit 38 reads the drug region image data 54 for each drug 12 in the initial illumination direction from the drug region image memory 49. Then, the feature image extraction unit 38 performs an edge detection process for each drug region image data item 54 to extract the feature image data 58 from each drug region image data item 54, and stores the extracted feature image data 58 in the feature image memory 50 (Step S8, a feature image extraction step). In this way, the feature image data 58 for each drug 12 in the initial illumination direction is stored in the feature image memory 50.

After the feature image data 58 for each drug 12 in the initial illumination direction is newly stored in the feature image memory 50, the illumination control unit 35 controls the floodlight 19 such that the illumination direction is switched to the next illumination direction which is rotated, for example, 90° from the initial illumination direction (No in Step S9 and Step S10, an illumination control step). Then, a set of the point light sources 25 corresponding to the initial illumination direction is turned off and a set of the point light sources 25 corresponding to the next illumination direction is turned on. The drug 12 in the light source holding unit 24 is illuminated in the next illumination direction (Step S5).

After the illumination direction is switched, the process from Step S5 to Step S8 is repeatedly performed. Then, the capture of the image of the drug 12 illuminated in the next illumination direction, the storage of the captured image data 28, and the storage of the drug region image data 54 and the feature image data 58 for each drug 12 in the next illumination direction are performed.

Then, until the capture of the image of the drug 12 in all of the four illumination directions is completed (YES in Step S9), the process from Step S5 to Step S10 is repeatedly performed. In this way, the four-direction feature image data 58 for each of the drugs 12 corresponding to one packet is stored in the feature image memory 50.

After the four-direction feature image data 58 for each of the drugs 12 corresponding to one packet is stored in the feature image memory 50, the feature image integration unit 39 reads the four-direction feature image data 58 for each drug 12 from the feature image memory 50. Then, the feature image integration unit 39 integrates the four-direction feature image data 58 for each drug 12 to generate the integrated image data 60 for each drug 12 and stores the integrated image data 60 in the integrated image memory 51 (Step S11, a feature image integration step). In this way, the integrated image data 60 for each of the drugs 12 corresponding to one packet is stored in the integrated image memory 51.

After the integrated image data 60 for each of the drugs 12 corresponding to one packet is newly stored in the integrated image memory 51, the drug recognition unit 43 reads the integrated image data 60 for each drug 12 from the integrated image memory 51. In addition, the drug recognition unit 43 discriminates the stamped character 14 on each drug 12 which is recorded in the dispensing information 62 acquired by the dispensing information acquisition unit 41 on the basis of the dispensing information 62, with reference to the drug DB 42.

Then, the drug recognition unit 43 compares the discrimination result of the stamped character 14 based on the dispensing information 62 with each integrated image data item 60 to recognize the stamped character 14 included in each integrated image data item 60. The comparison between the discrimination result of the stamped character 14 and the dispensing information 62 makes it possible to reduce errors in the recognition of the stamped character 14 even in a case in which the shape of the stamped character 14 included in each integrated image data item 60 is incomplete, for example, even in a case in which a portion of the stamped character 14 is distorted or chipped off. Then, the drug recognition unit 43 recognizes the type of each drug 12 in the first packet 11 on the basis of each stamped character 14 recognized from each integrated image data item 60, with reference to the drug DB 42, and outputs the recognition result to the inspection unit 44 (Step S12, a recognition step).

In a case in which there is a drug 12 in which the stamped character 14 included in the integrated image data 60 is too unclear to be recognized, the drug recognition unit 43 outputs the determination result indicating that the recognition of the drug 12 has failed to the display unit 45.

The inspection unit 44 collates the result of recognizing the type of each drug 12 in the first packet 11 which is input from the drug recognition unit 43 with the type of each drug 12 in the first packet 11 which is recorded in the dispensing information 62 (Step S13). Then, the inspection unit 44 outputs the collation result to the display unit 45 and the storage unit 46.

The display unit 45 displays the collation result input from the inspection unit 44 (Step S14). At that time, in a case in which the collation result shows the mismatch therebetween, the display unit 45 displays the type name of the corresponding drug 12 to issue a warning to, for example, the pharmacist who performs dispensing inspection. In a case in which the determination result indicating that the recognition of the drug 12 has failed is input from the drug recognition unit 43, the display unit 45 displays the determination result to issue a warning to, for example, the pharmacist who performs dispensing inspection.

In this way, the recognition and inspection of the type of drug 12 packaged in the first packet 11 are completed. In addition, the collation result corresponding to the first packet 11 which is input from the inspection unit 44 and the four-direction captured image data 28 in the storage unit 46 are stored in the captured image memory 48.

Then, the transport mechanism 18 intermittently transports the tray 17 in the longitudinal direction to set the second packet 11 in the light source holding unit 24 (YES in Step S15, Step S16, and Step S3). Then, the process from Step S3 to Step S14 is repeatedly performed to recognize and inspect the type of drug 12 packaged in the second packet 11. Until the recognition and inspection of the type of drug 12 packaged in all of the series of packets 11 are completed, the process from Step S3 to Step S14 is repeatedly performed (NO in Step S15).

[Operation and Effect of Drug Inspection Device According to First Embodiment]

As such, the drug inspection device 10 captures the image of the drug 12 while switching the direction in which the drug 12 is illuminated and recognizes the stamped character 14 on the drug 12 on the basis of the integrated image data 60 obtained by integrating the feature image data 58 extracted from the captured image data 28 in each illumination direction. Therefore, it is possible to accurately recognize the stamped character 14 on the drug 12, without being affected by the illumination direction or the surface shape of the drug. As a result, it is possible to accurately recognize the type of drug 12 having the stamped character 14 on the surface thereof.

[Drug Inspection Device According to Second Embodiment]

Next, a drug inspection device 65 according to a second embodiment of the invention will be described with reference to FIG. 8. The drug inspection device 10 according to the first embodiment rotates the illumination direction of the floodlight 19 in the circumferential direction of the light source holding unit 24 at an interval of 90°. However, other illumination conditions may be switched in order to capture the image of the drug 12 under the illumination conditions suitable for recognizing the stamped character 14. Therefore, the drug inspection device 65 switches (rotates) the illumination direction under each sub-illumination condition while switching the sub-illumination conditions, which are illumination conditions other than the rotation of the illumination direction.

The drug inspection device 65 has the same basic structure as the drug inspection device 10 according to the first embodiment except that it includes an illumination control unit 35A and a masking unit 67. Therefore, components having the same functions and structures as those in the drug inspection device 10 according to the first embodiment are denoted by the same reference numerals and the description thereof will not be repeated.

The illumination control unit 35A controls the emission of illumination light by the floodlight 19 and the backlight 20 under the control of the overall control unit 30 to switch the illumination direction under each sub-illumination condition while switching the sub-illumination conditions as the switching of the illumination conditions of the drug 12. The sub-illumination conditions include various conditions (see FIG. 9) such as a "high angle", a "low angle", a "backlight", "light amount adjustment", "switching the illumination direction four times", and "switching the illumination direction eight times". In addition, the switching of the sub-illumination conditions means the switching of at least one of the various conditions.

For the sub-illumination condition "high angle", only the point light source 25 provided in the upper end portion of the outside surface of the light source holding unit 24 is turned on such that illumination light is incident on the drug 12 in the light source holding unit 24 at a high incident angle. Inversely, for the sub-illumination condition "low angle", only the point light source 25 provided in the lower end portion of the outside surface is turned on such that illumination light is incident on the drug 12 in the light source holding unit 24 at a low incident angle. As such, for the sub-illumination conditions "high angle" and "low angle", the incident angles of the illumination light (the height of illumination) are different from each other. Therefore, it is possible to adjust the intensity of a shadow (shadow image 56) generated in the stamped character 14. As a result, it is possible to increase the intensity of the shadow generated in the stamped character 14, using the sub-illumination conditions "high angle" and "low angle", even when, for example, the surface shape of the drug 12, the shape and position of the stamped character 14 on the drug, and the position of the drug 12 in the light source holding unit 24 are not constant.

For the sub-illumination condition "backlight", the backlight 20 illuminates the drug 12 in the light source holding unit 24 from the rear side. This makes it easy to particularly recognize the color or shape of the drug 12 such as a black tablet or a transparent capsule. Therefore, it is possible to accurately extract the drug region image data 54 corresponding to, for example, a black tablet or a transparent capsule from the captured image data 28.

For the sub-illumination condition "light amount adjustment", the amount of illumination light emitted from the point light source 25 is adjusted. For example, in a case in which a white tablet is included in the drugs 12 in the light source holding unit 24 on the basis of the dispensing information 62, the amount of illumination light is reduced to be less than a normal set value, which makes it easy to recognize the color or shape of the white tablet. Therefore, it is possible to accurately extract the drug region image data 54 corresponding to the white tablet from the captured image data 28. In addition, it is easy to recognize the shadow of the stamped character 14 and thus it is possible to extract the feature image data 58 from the drug region image data 54.

For example, in a case in which a black tablet is included in the drugs 12 in the light source holding unit 24, the amount of illumination light increases to be more than the normal set value, which makes it easy to recognize the color or shape of the black tablet. Therefore, it is possible to accurately extract the drug region image data 54 corresponding to the black tablet from the captured image data 28. In addition, since the surface of the black tablet is black, it is difficult to detect the shadow of the stamped character 14. However, since the amount of illumination light increases, the possibility of success in extracting the feature image data 58 from the drug region image data 54 increases.

It is possible to determine whether a white tablet or a black tablet is included in the drugs 12 in the light source holding unit 24, on the basis of the dispensing information 62 acquired by the dispensing information acquisition unit 41.

The sub-illumination condition "switching the illumination direction four times" means that the number of times the illumination direction of the floodlight 19 is switched is set to 4 and the illumination direction is switched four times as described in the first embodiment. In addition, the sub-illumination condition "switching the illumination direction eight times" means that the number of times the illumination direction of the floodlight 19 is switched is set to 8 and the illumination direction is switched eight times. When the number of times the illumination direction is switched increases (here, from 4 to 8), the definition of the contour of the stamped character 14 in the integrated image data 60 increases. Therefore, the drug recognition unit 43 can accurately recognize the stamped character 14.

Figure 9:
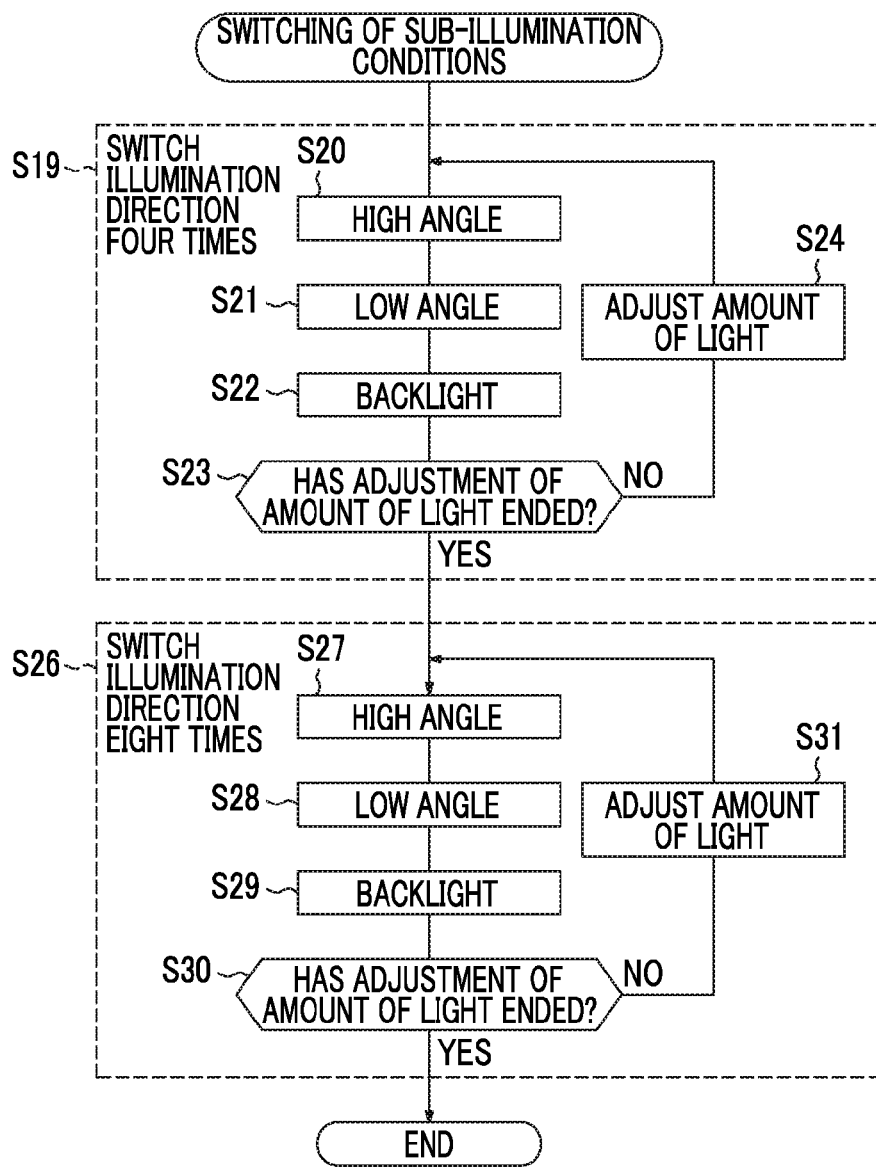
FIG. 9 is a diagram illustrating the switching of sub-illumination conditions by an illumination control unit.

In FIG. 9 illustrating an example of a sub-illumination condition switching process, first, the illumination control unit 35A sets the sub-illumination conditions of the floodlight 19 to "switching the illumination direction four times" and "high angle" (Steps S19 and S20). Then, the illumination control unit 35A sequentially turns on and off every other point light source among eight point light sources 25 provided in the upper end portion of the outside surface of the light source holding unit 24 to sequentially switch the illumination direction to four directions. Therefore, illumination light can be sequentially incident on the drug 12 in the light source holding unit 24 at a high incident angle in four directions.

Then, the illumination control unit 35A switches the sub-illumination condition from "high angle" to "low angle" (Step S21). Then, the illumination control unit 35A sequentially turns on and off every other point light source among eight point light sources 25 provided in the lower end portion of the outside surface of the light source holding unit 24 to sequentially switch the illumination direction to four directions. Therefore, illumination light can be sequentially incident on the drug 12 in the light source holding unit 24 at a low incident angle in four directions.

After the illumination direction is switched four times under the sub-illumination condition "low angle", the illumination control unit 35A switches the sub-illumination condition from "low angle" to "backlight" (Step S22). Then, the illumination control unit 35A switches the illumination direction of the floodlight 19 four times, with illumination light emitted from the backlight 20, similarly to the first embodiment.

After the illumination direction is switched four times under the sub-illumination condition "backlight", the illumination control unit 35A determines whether a white tablet or a black tablet is included in the drugs 12 in the light source holding unit 24, on the basis of the dispensing information 62 acquired by the dispensing information acquisition unit 41. In a case in which a white tablet or a black tablet is included in the drugs 12 in the light source holding unit 24, the illumination control unit 35A performs "light amount adjustment" (NO in Step S23 and Step S24). For example, in a case in which a white tablet is included in the drugs 12 in the light source holding unit 24, the amount of illumination light emitted from each point light source 25 is reduced to be less than the normal set value. In contrast, in a case in which a black tablet is included in the drugs 12 in the light source holding unit 24, the amount of illumination light emitted from each point light source 25 increases to be greater than the normal set value.

Then, the illumination control unit 35A repeatedly performs the process from Step S20 to Step S22 again, using the adjusted amount of illumination light, to switch the illumination direction four times under each sub-illumination condition while sequentially switching the sub-illumination conditions. In a case in which both the white tablet and the black tablet are included in the drugs 12 in the light source holding unit 24, "light amount adjustment" is performed two times and the process from Step S20 to Step S22 is repeatedly performed in a state in which the amount of illumination light is reduced and a state in which the amount of illumination light increases.

After "light amount adjustment" ends (YES in Step S23), the illumination control unit 35A switches the sub-illumination condition from "switching the illumination direction four times" to "switching the illumination direction eight times" (Step S26). Then, the illumination control unit 35A switches the illumination direction eight times under each sub-illumination condition while switching the sub-illumination conditions in the order of "high angle", "low angle", and "backlight", similarly to "switching the illumination direction four times" (Steps S27, S28, and S29). When the sub-illumination condition "high angle" is set, the illumination control unit 35A sequentially turns on and off the point light sources 25 provided in the upper end portion of the outside surface. When the sub-illumination condition "low angle" is set, the illumination control unit 35A sequentially turns on and off the point light sources 25 provided in the lower end portion of the outside surface. When the sub-illumination condition "backlight" is set, the illumination control unit 35A sequentially turns on and off a set of the point light sources 25.

Then, in a case in which a white tablet or a black tablet is included in the drugs 12 in the light source holding unit 24, the illumination control unit 35A performs "light amount adjustment", similarly to "switching the illumination direction four times" (NO in Step S30 and Step S31). Then, the illumination control unit 35A repeatedly performs the process from Step S20 to Step S22 again, using the adjusted amount of illumination light, to switch the illumination direction eight times under each sub-illumination condition while sequentially switching the sub-illumination conditions. In this way, the switching of the sub-illumination conditions ends (YES in Step S30).

As such, in a case in which the illumination direction is switched under the sub-illumination condition while the sub-illumination conditions are being switched, the acquisition of the captured image data 28, the extraction of the drug region image data 54, the extraction of the feature image data 58, the generation of the integrated image data 60, and the recognition of the stamped character 14 and the type of drug 12 are performed, similarly to the first embodiment. In addition, under the sub-illumination condition "switching the illumination direction eight times", the recognition of the stamped character 14 and the type of drug 12 can be basically the same as that under the sub-illumination condition "switching the illumination direction four times" except that the captured image data 28, the drug region image data 54, and the feature image data 58 are obtained in eight directions.

Before switching to all of the sub-illumination conditions is completed, for example, in a case in which the drug recognition unit 43 has succeeded in the recognition of all of the drugs 12 in Step S21, the illumination control unit 35A does not perform the switching of the sub-illumination conditions after Step S22. That is, the illumination control unit 35A repeatedly performs the switching of the sub-illumination conditions and the switching of the illumination direction under a new sub-illumination condition until the drug recognition unit 43 succeeds in recognizing all of the drugs 12.

Figure 8:
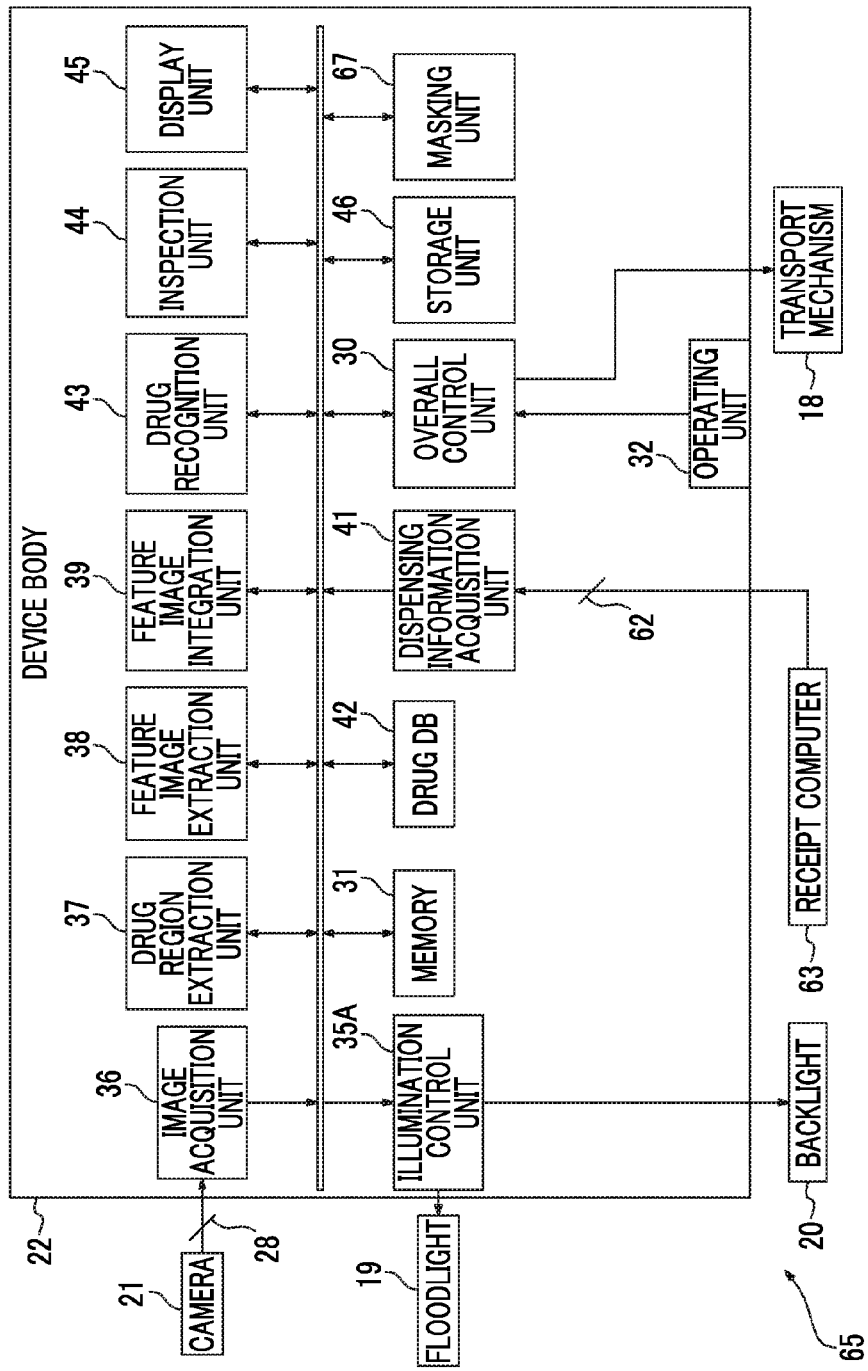
FIG. 8 is a block diagram illustrating the electrical structure of a drug inspection device according to a second embodiment.

As illustrated in FIGS. 8 and 10, the masking unit 67 performs a masking process (which is hatched) of masking a region corresponding to the drug 12, of which the type has been successfully recognized by the drug recognition unit 43, for the captured image data 28 which is newly stored in the captured image memory 48. For example, in a case in which the drug recognition unit 43 has succeeded in recognizing two drugs 12 among four drugs 12 under a first sub-illumination condition (reference numeral 309), a masking process of masking regions corresponding to the two drugs 12 which have been successfully recognized is performed for the captured image data 28 which is obtained under a second sub-illumination condition (reference numeral 310).

In a case in which the masking process is performed by the masking unit 67, the drug region extraction unit 37 extracts the drug region image data 54 from a region other than the masked regions in the captured image data 28. Therefore, the feature image extraction unit 38 extracts the feature image data 58 from a region other than the masked region in the captured image data 28.

[Operation of Drug Inspection Device According to Second Embodiment]

Figure 11:
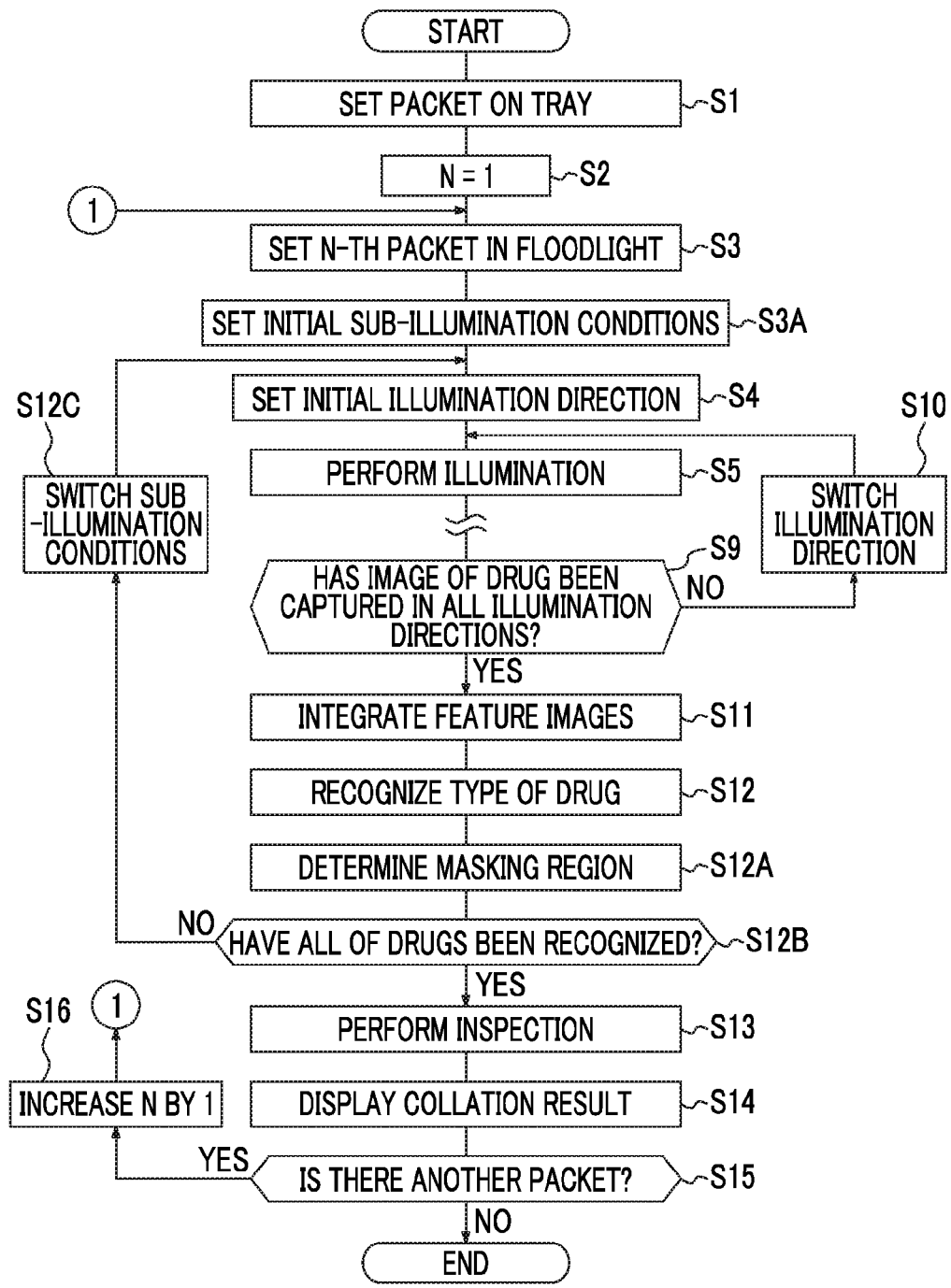
FIG. 11 is a flowchart illustrating the flow of an inspection process of the drug inspection device according to the second embodiment.

Next, the operation of the drug inspection device 65 having the above-mentioned structure will be described with reference to FIG. 11. When the process from Step S1 to Step S3 is performed as described in the first embodiment, the first (N=1) packet 11 is set in the light source holding unit 24.

After the setting of the first packet 11 is completed, the illumination control unit 35A sets the initial sub-illumination conditions to "switching the illumination direction four times" and "high angle", as illustrated in FIG. 9 (Step S3A). The process from Step S4 to Step S12 is performed under the initial conditions similarly to the first embodiment and the drug recognition unit 43 recognizes the type of each drug 12 in the first packet 11.

The masking unit 67 determines a region corresponding to the drug 12, of which the type has been successfully recognized by the drug recognition unit 43, in the captured image data 28 as a masking region to be subjected to the masking process (Step S12A).

Then, the illumination control unit 35A switches the sub-illumination conditions as illustrated in FIG. 9. Specifically, the illumination control unit 35A switches the sub-illumination conditions from "high angle" to "low angle" (NO in Step S12B and Step S12C). Then, the process from Step S4 to Step S12 is performed under a new sub-illumination condition similarly to the first embodiment and the drug recognition unit 43 recognizes the type of each drug 12 in the first packet 11 again.

At that time, the masking unit 67 performs a masking process of masking the determined masking region for the captured image data 28 which is newly stored in the captured image memory 48. Since the drug region image data 54 or the feature image data 58 is not extracted from the masking region of the captured image data 28, the type of the drug 12 which has been successfully recognized is prevented from being recognized again. As a result, it is possible to reduce the time required to recognize the drug 12 and to reduce the load of a calculation process.

The masking unit 67 determines a region corresponding to the new drug 12, of which the type has been successfully recognized by the drug recognition unit 43, in the captured image data 28 as a new masking region (Step S12A).

Then, until the recognition of the types of all of the drugs 12 in the first packet 11 succeeds, the switching of the sub-illumination conditions illustrated in FIG. 9, the switching of the illumination direction under a new sub-illumination condition, the acquisition of the captured image data 28, the extraction of the drug region image data 54 and the feature image data 58, the generation of the integrated image data 60, and the recognition of the stamped character 14 and the type of drug 12 are repeatedly performed (Steps S4 to S12C).

When the recognition of the types of all of the drugs 12 in the first packet 11 has succeeded (YES in Step S12B), the inspection (collation) process of the inspection unit 44 and the display of the collation result by the display unit 45 described in the first embodiment are performed (Steps S13 and S14). In a case in which there is a drug 12 which has not been recognized by the switching of all of the sub-illumination conditions illustrated in FIG. 9, information indicating the fact is displayed on the display unit 45.

In this way, the recognition and inspection of the types of drugs 12 packaged in the first packet 11 are completed. Then, until the recognition and inspection of the types of drugs 12 packaged in all of a series of packets 11 are completed, the process from Step S3 to Step S14 is repeatedly performed (Steps S15 and S16).

[Operation and Effect of Drug Inspection Device According to Second Embodiment]

As such, the drug inspection device 65 performs the switching of various sub-illumination conditions, in addition to the switching of the illumination direction (the rotation of the illumination direction) described in the first embodiment. Therefore, it is possible to capture the image of the drug 12 under the illumination conditions that are suitable for recognizing the stamped character 14. As a result, the probability of success in recognizing the stamped character 14 on the drug 12 (that is, recognizing the type of drug 12) is higher than that in the first embodiment. In addition, it is possible to accurately recognize the stamped character 14 on the drug 12 (type of drug 12).

[Structure of Drug Inspection Device According to Third Embodiment]

Figure 12:
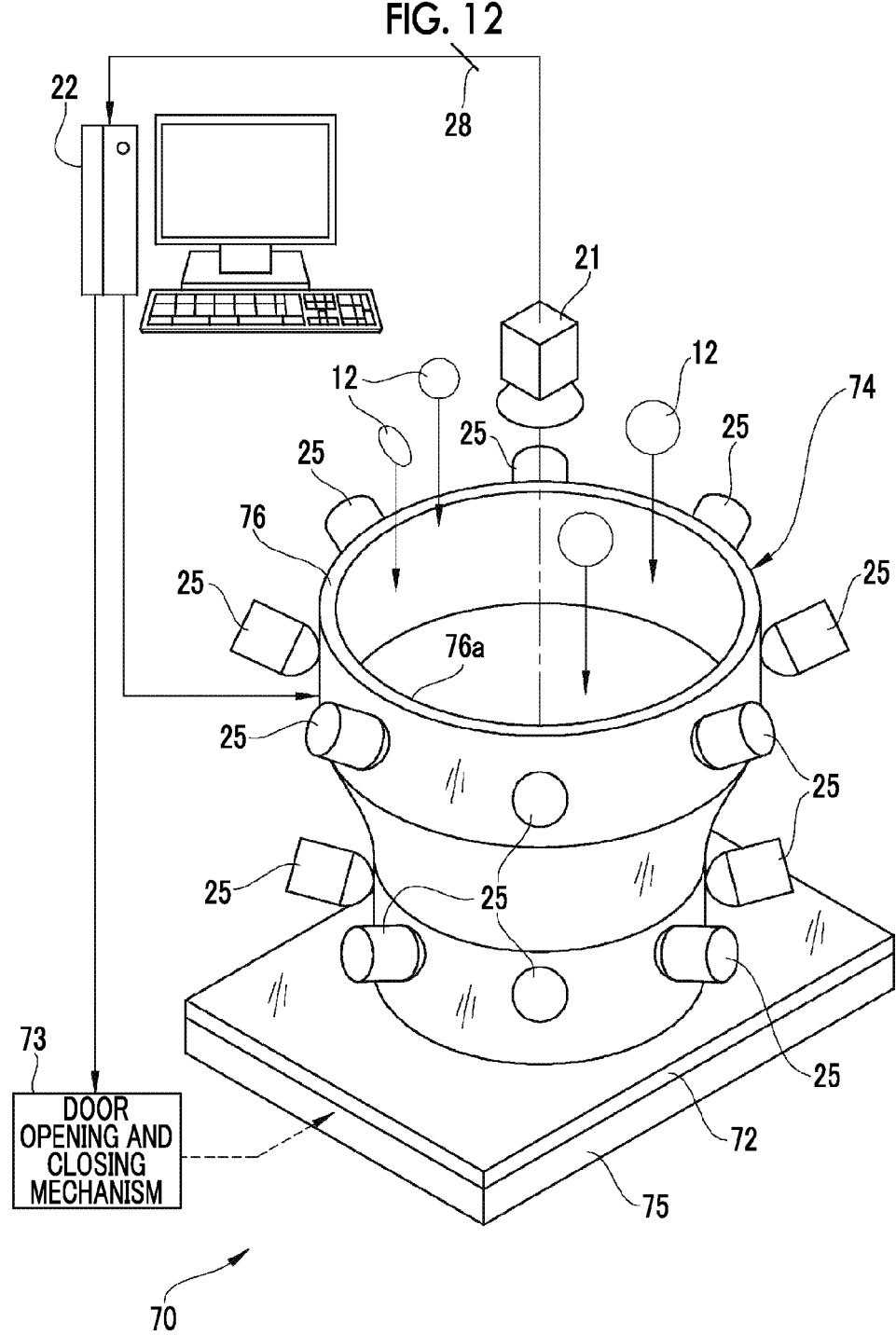
FIG. 12 is a perspective view illustrating a drug inspection device according to a third embodiment.
Figure 13:
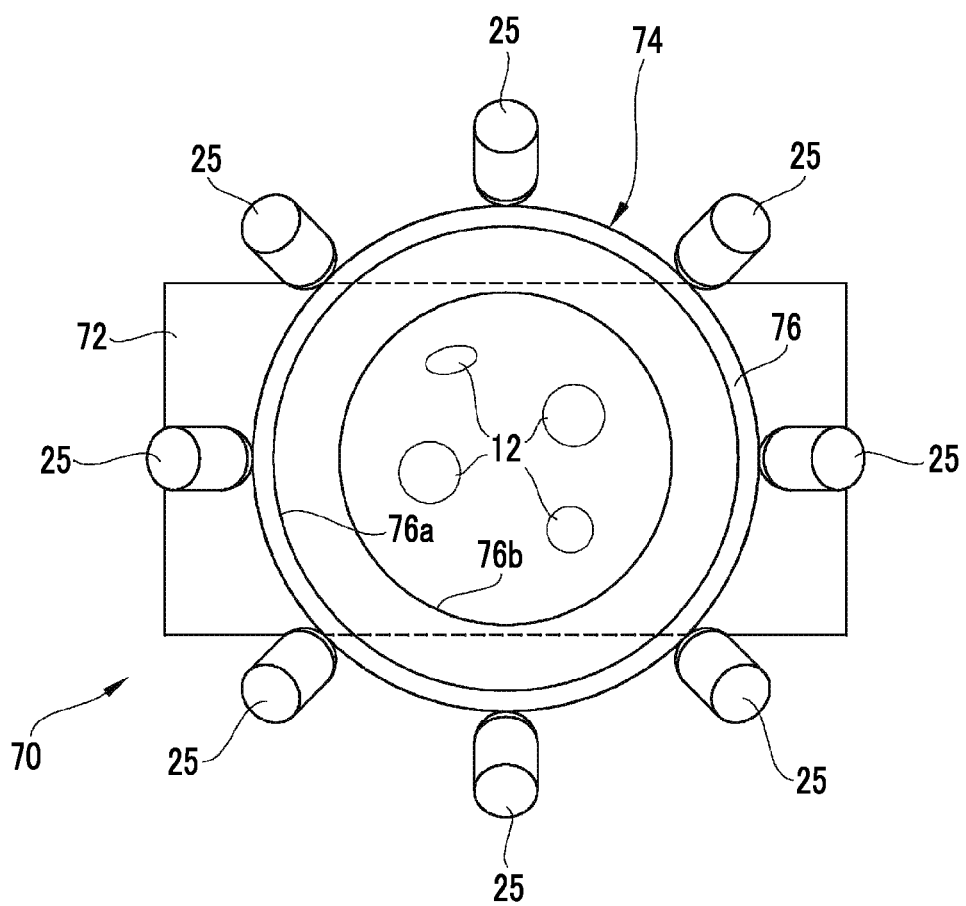
FIG. 13 is a top view illustrating an inspection pod of the drug inspection device illustrated in FIG. 12.

Next, a drug inspection device 70 according to a third embodiment of the invention will be described with reference to FIGS. 12 and 13. The drug inspection devices 10 and 65 according to the above-described embodiments recognize the drug 12 after the drug 12 is packaged in the packet 11. However, the drug inspection device 70 recognizes the drug 12 before the drug 12 is packaged in the packet 11. The drug inspection device 70 is provided in a packaging device (not illustrated). In addition, the packaging device has the functions of the drug inspection device 70.

The drug inspection device 70 has the same basic structure as the drug inspection device 10 according to the first embodiment except that it includes a transparent door 72, a door opening and closing mechanism 73, a transparent inspection pod (illumination unit) 74, and a backlight 75, instead of the tray 17, the transport mechanism 18, and the floodlight 19 according to the first embodiment. Therefore, components having the same functions and structures as those in the drug inspection device 10 according to the first embodiment are denoted by the same reference numerals and the description thereof will not be repeated.

For example, the door 72 is provided on a drug passage that is connected to a hopper (not illustrated) through which drugs corresponding to one packet are packaged in the packet 11 in the packaging device. The drug passage is opened and closed by the door 72.

The door opening and closing mechanism 73 shifts the door 72 between a closed position where the drug passage is closed and an open position (see FIG. 14) where the door 72 is evacuated from the drug passage to switch the opening and closing of the door 72 under the control of the overall control unit 30.

The inspection pod 74 is set on the upper surface of the door 72 at the closed position in the drawings. Drugs 12 corresponding to one packet are put into the inspection pod 74. The drugs 12 corresponding to one packet which are put into the inspection pod 74 are placed on the door 72 in the inspection pod 74. Then, the inspection pod 74 illuminates the drugs 12 corresponding to one packet which are put thereinto. The inspection pod 74 includes a pod body 76 and a plurality of point light sources 25 which are attached to the pod body 76.

The pod body 76 is formed in a substantially cylindrical shape. In addition, an upper opening portion 76a which is provided at the top of the pod body 76 in FIG. 12 is formed such that the area thereof is greater than the area of a lower opening portion 76b which is provided at the bottom of the pod body 76. Therefore, at least a portion of the outside surface of the pod body 76 has an inclined surface.

Eight point light sources 25 are attached to a lower end portion of the outside surface of the pod body 76 at equal intervals along the circumferential direction and eight point light sources 25 are attached to an upper end portion of the outside surface of the pod body 76 at equal intervals along the circumferential direction. Therefore, the inspection pod 74 has the same basic structure as the floodlight 19 according to the first embodiment. Similarly to the first embodiment, it is possible to control the turn-on and turn-off each of the 16 point light sources to switch the direction in which the drugs 12 in the inspection pod 74 are illuminated. That is, as described in the first embodiment, it is possible to sequentially switch the illumination direction to four directions or eight directions.

The backlight 75 is fixed to the lower surface of the door 72 in the drawings. The backlight 75 illuminates the drug 12 which is located in the inspection pod 74 and on the door 72 through the transparent door 72 from the rear side.

The camera 21 is provided above the upper opening portion 76a of the inspection pod 74. The camera 21 captures the image of the drug 12 in the inspection pod 74 through the upper opening portion 76a, generates captured image data 28, and outputs the captured image data 28 to the device body 22.

As such, the drug inspection device 70 according to the third embodiment illuminates the drug 12 in the inspection pod 74 which has the same basic structure as the floodlight 19 according to the first embodiment, using the inspection pod 74. Therefore, the device body 22 according to the third embodiment has the same basic structure as the device body 22 according to the first embodiment except that the overall control unit 30 controls the door opening and closing mechanism 73 such that the door 72 is opened and closed and the illumination control unit 35 controls the illumination of the inspection pod 74 and the backlight 75. As a result, similarly to the first embodiment, it is possible to perform the recognition of the type of drugs 12 (stamped character 14) corresponding to one packet in the inspection pod 74, the inspection (collation) process of the inspection unit 44, and the display of the collation result by the display unit 45, on the basis of the captured image data 28 in a plurality of illumination directions which is acquired from the camera 21.

Figure 14:
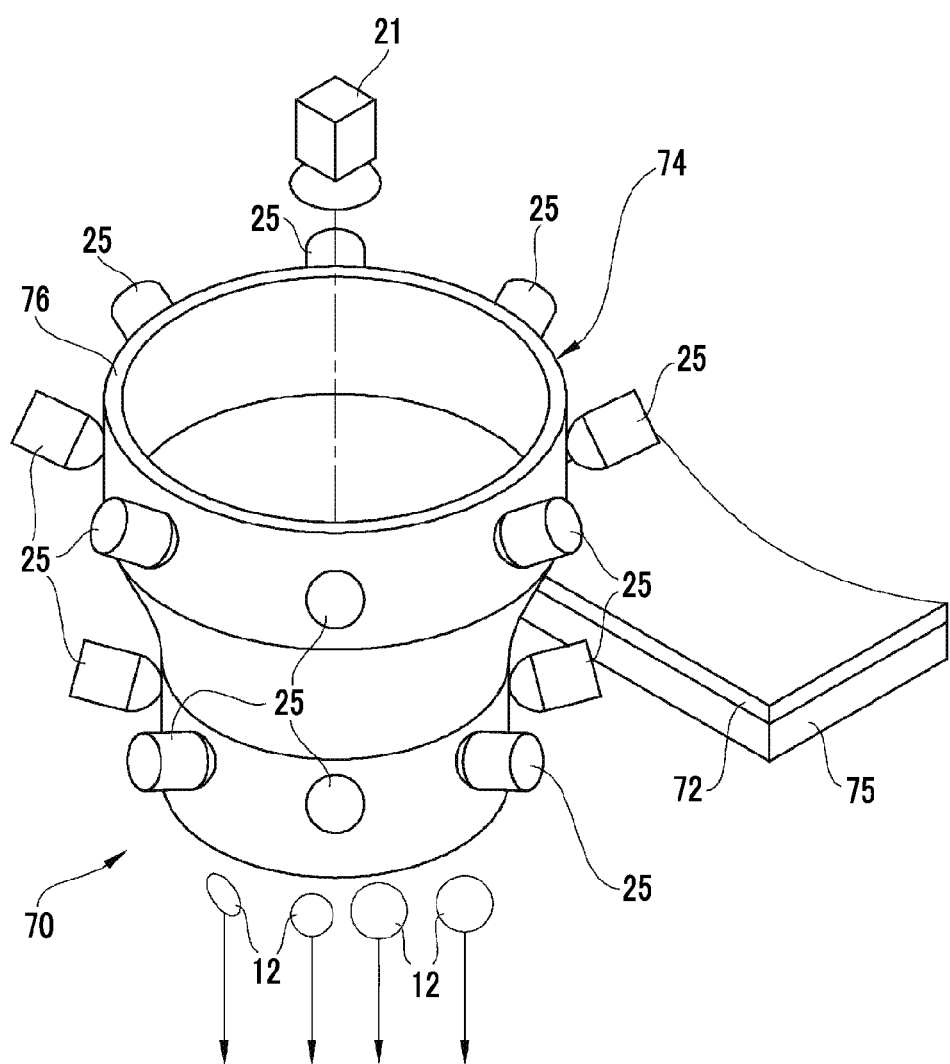
FIG. 14 is a diagram illustrating a state in which a door illustrated in FIG. 12 is moved from a closed position to an open position.

As illustrated in FIG. 14, in a case in which the recognition of the type of drugs 12 corresponding to one packet in the inspection pod 74 ends, the overall control unit 30 controls the door opening and closing mechanism 73 such that the door 72 is shifted to the open position. Then, the drug 12 in the inspection pod 74 is discharged into the drug passage and is then guided to the hopper.

[Operation of Drug Inspection Device According to Third Embodiment]

Figure 15:
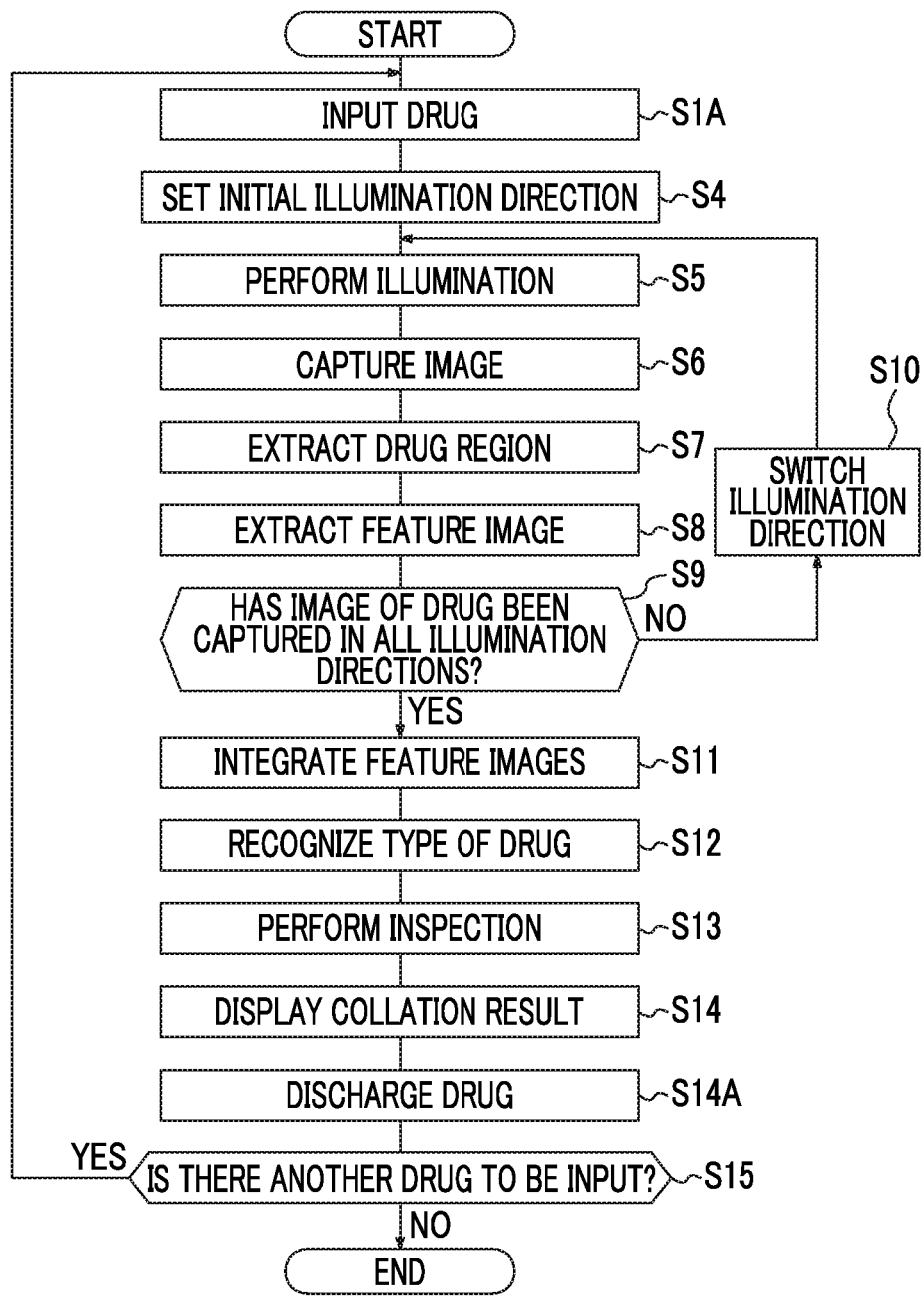
FIG. 15 is a flowchart illustrating the flow of an inspection process of the drug inspection device according to the third embodiment.

Next, the operation of the drug inspection device 70 having the above-mentioned structure will be described with reference to FIG. 15. First, the pharmacist puts the drugs 12 corresponding to one packet into the inspection pod 74 according to the dispensing information 62 (Step S1A). At that time, since the door 72 has been moved to the closed position in advance, the drugs 12 are placed on the door 72 in the inspection pod 74. Then, when an inspection start operation is performed through the operating unit 32, the overall control unit 30 operates each unit of the device body 22 to perform the process from Step S4 to Step S14 described in the first embodiment. Then, the types of the drugs 12 corresponding to one packet in the inspection pod 74 are recognized and the collation result of the inspection unit 44 is displayed on the display unit 45.

Then, the overall control unit 30 controls the door opening and closing mechanism 73 such that the door 72 is shifted to the open position and the drugs 12 in the inspection pod 74 are discharged into the drug passage (Step S14A). Then, the drugs 12 in the inspection pod 74 are put into the drug passage and are then guided to the hopper. In a case in which the collation result of the inspection unit 44 shows the mismatch between the types of drugs or there is a drug 12 of which the recognition has failed, the shift of the door 72 may be prevented.

Then, whenever the drugs 12 corresponding to one packet are put into the inspection pod 74, the process from Step S4 to Step S14A is repeatedly performed (Step S15).

[Operation and Effect of Drug Inspection Device According to Third Embodiment]

The drug inspection device 70 according to the third embodiment performs the illumination of the drug 12 and the switching of the illumination direction which are basically the same as those in the first embodiment. Therefore, the same effect as that described in the first embodiment is obtained.

[Other Examples of Structure of Drug Inspection Device According to Third Embodiment]

In the third embodiment, only the switching (rotation) of the illumination direction is performed, similarly to the first embodiment. However, as described in the second embodiment, the illumination direction may be switched under each sub-illumination condition while the sub-illumination conditions are being switched. In this case, the flow of the basic process is the same as that in the second embodiment except for the input and discharge of the drug 12. Therefore, the detailed description thereof will not be repeated here.

In the third embodiment, the backlight 75 is fixed to the lower surface of the door 72 in the drawings. However, for example, a door 78 which is a light guide plate illustrated in FIG. 16 may be used. The door 78 is shifted between the closed position and the open position by the door opening and closing mechanism 73 (not illustrated), similarly to the door 72.

Figure 16:
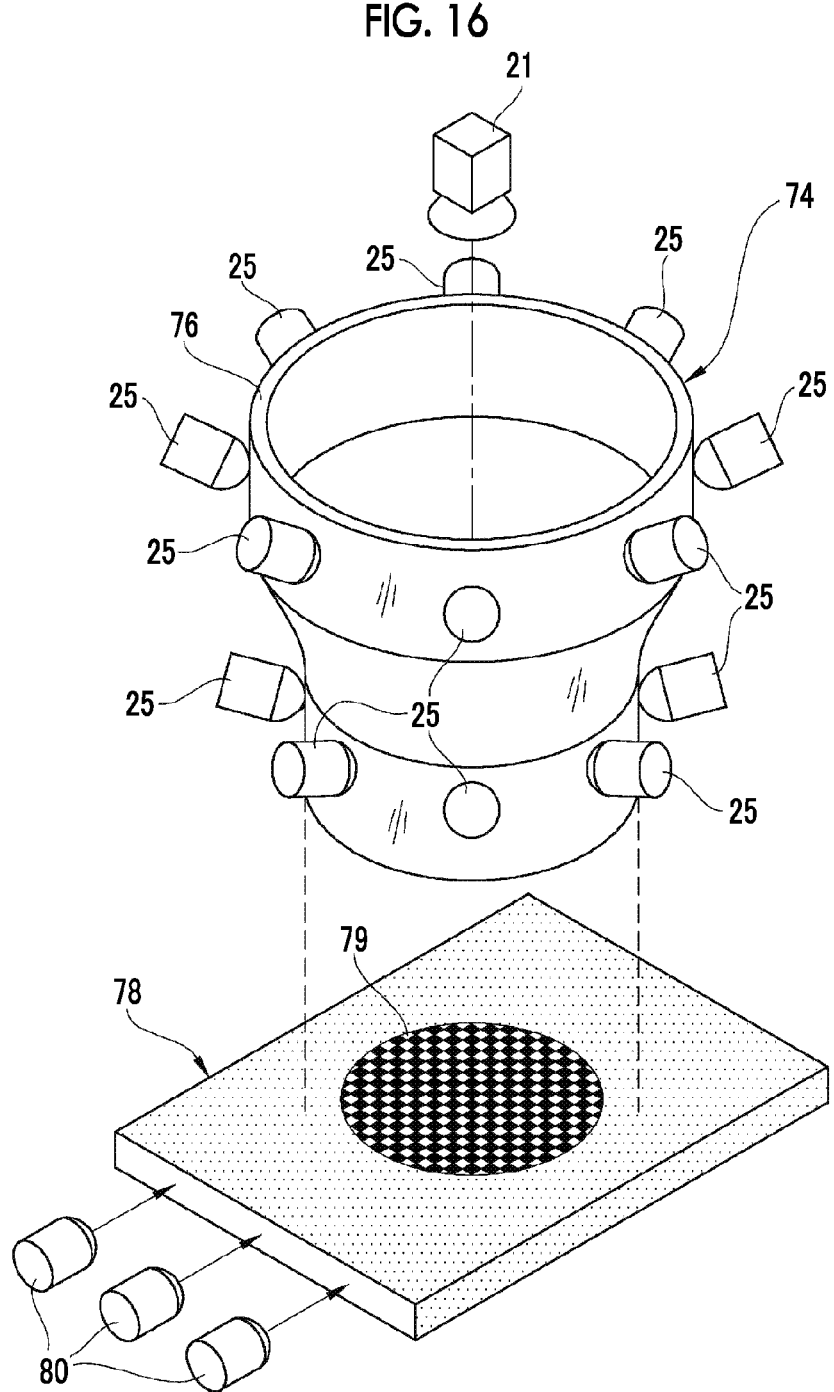
FIG. 16 is a perspective view illustrating another example of the door according to the third embodiment.

The entire region of the door 78 except for one side surface and a pod set region of the upper surface in which the inspection pod 74 is set is shielded (a dotted portion in FIG. 16). In addition, a white and black checkered pattern 79 is formed in the pod set region on the upper surface of the door 78.

Backlight light sources 80 are provided at a position facing one side surface of the door 78. Illumination light emitted from the backlight light sources 80 can be incident on one side surface of the door 78 and can be emitted from a white pattern of the white and black pattern 79 to the upper side. Therefore, it is possible to illuminate the drug 12 which is placed on the door 78 in the inspection pod 74 from the rear side. When the backlight light source 80 is turned off, the background of the drug 12 on the door 78 can be darkened by a black pattern of the white and black pattern 79. In addition, light sources of a plurality of colors may be provided as the backlight light sources 80 and the color of illumination light for a backlight may be switched.

Figure 17:
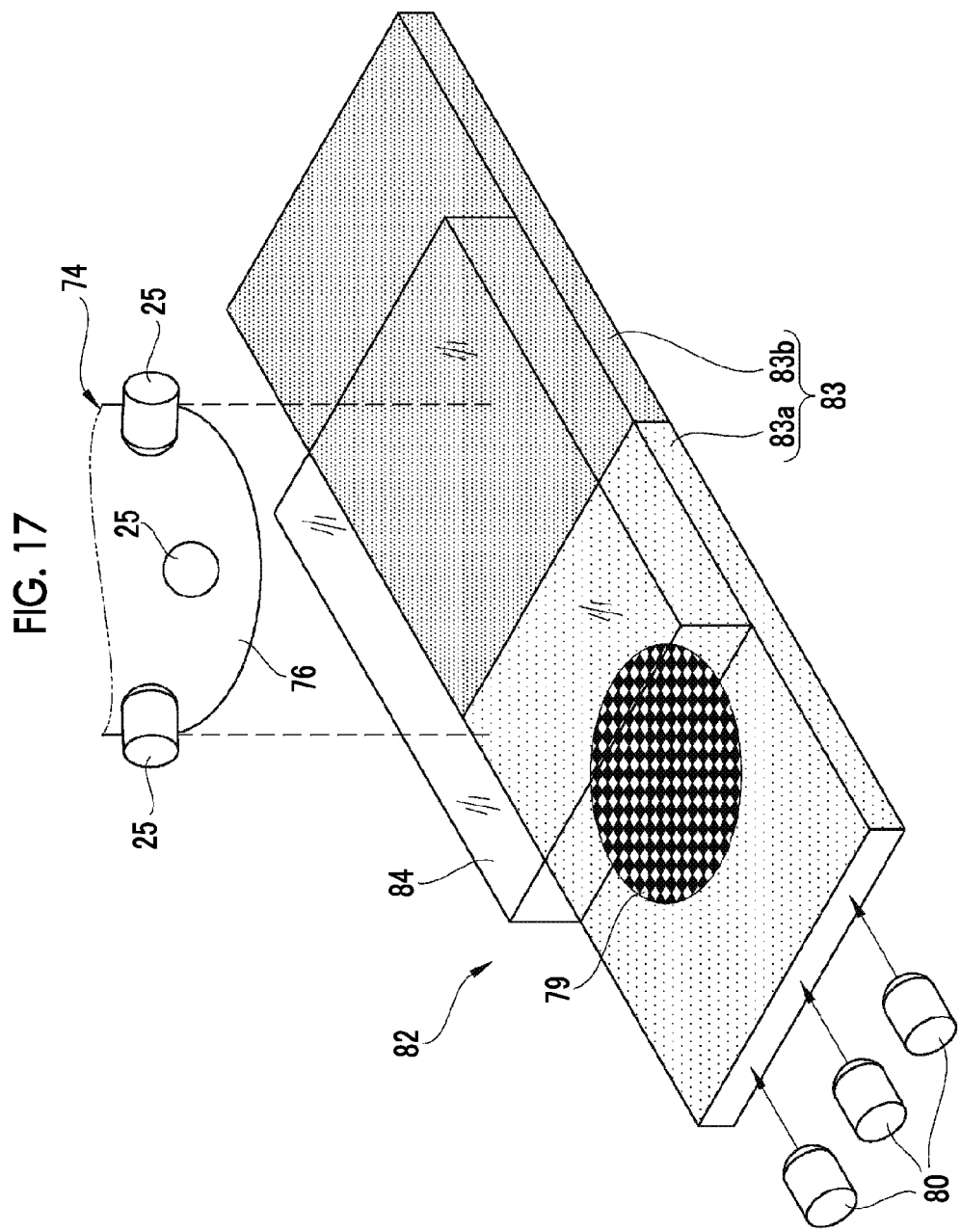
FIG. 17 is a perspective view illustrating still another example of the door according to the third embodiment.

For example, a door 82 including two plates illustrated in FIG. 17 may be used instead of the door 72 according to the third embodiment. Similarly to the door 72, the door 82 is integrally shifted between the closed position and the open position by the door opening and closing mechanism 73 (not illustrated).

The door 82 includes a lower plate 83 and an upper transparent plate 84 which is slidably provided on the lower plate 83. The lower plate 83 is formed by connecting a light guide plate 83a which has the same structure as the door 78 illustrated in FIG. 16 and a light shielding plate 83b. Illumination light from the backlight light sources 80 is incident on one side surface of the light guide plate 83a and is emitted from the white pattern of the white and black pattern 79 to the upper side.

The inspection pod 74 is set on the surface of the upper plate 84. The upper plate 84 is slid between an illumination position on the light guide plate 83a and a light shielding position on the light shielding plate 83b by an upper plate shift mechanism (not illustrated). Therefore, when backlight illumination is performed, the upper plate 84 is set to the illumination position and illumination light from the backlight light sources 80 is incident on one side surface of the light guide plate 83a. In this way, it is possible to illuminate the drug 12 which is placed on the upper plate 84 in the inspection pod 74 from the rear side. In a case in which backlight illumination is stopped, the upper plate 84 can be set to the light shielding position to darken the background of the drug 12 on the upper plate 84.

[Drug Inspection Device According to Fourth Embodiment]

Figure 18:
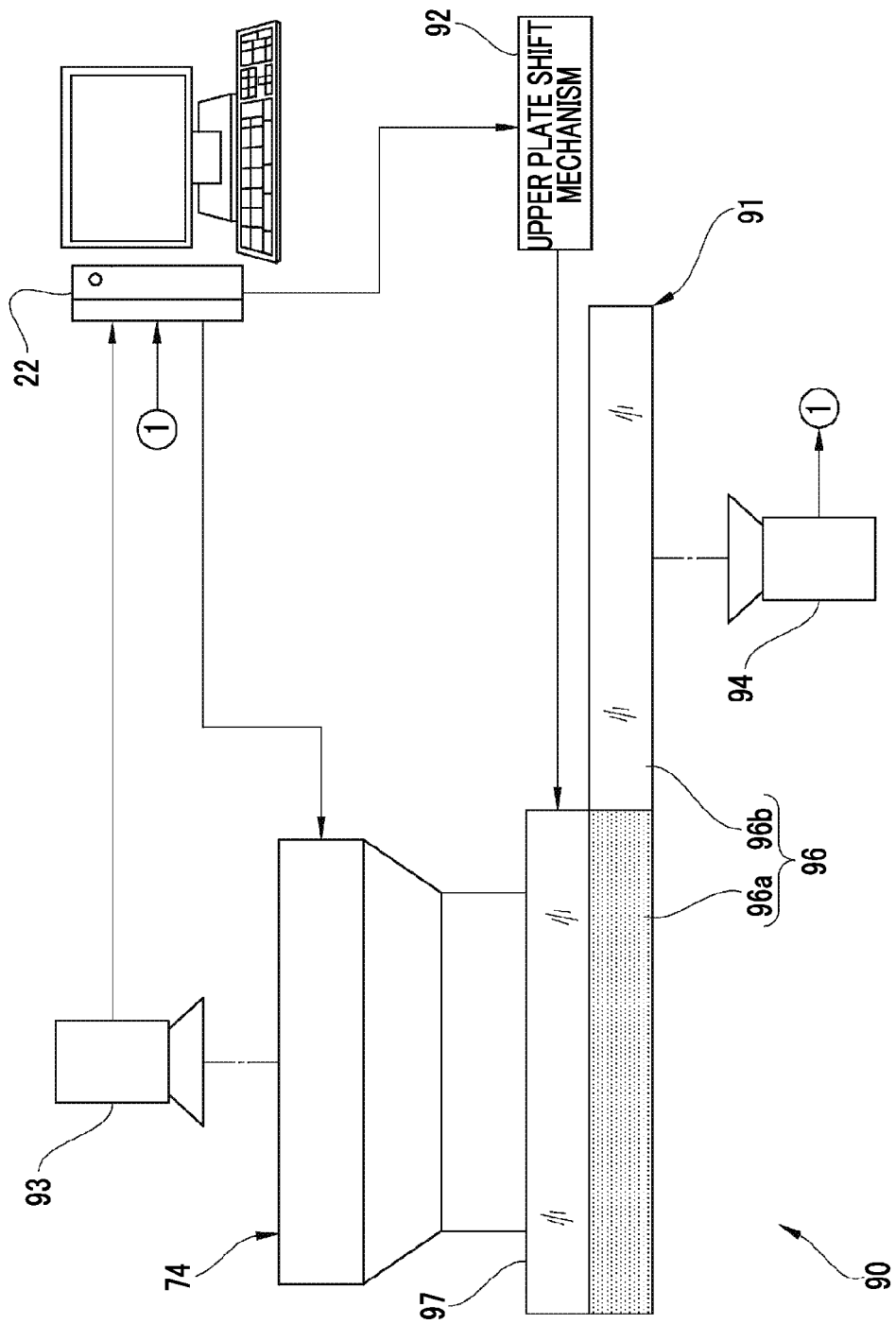
FIG. 18 is a diagram schematically illustrating a drug inspection device according to a fourth embodiment in which an upper plate is moved to a first position.
Figure 19:
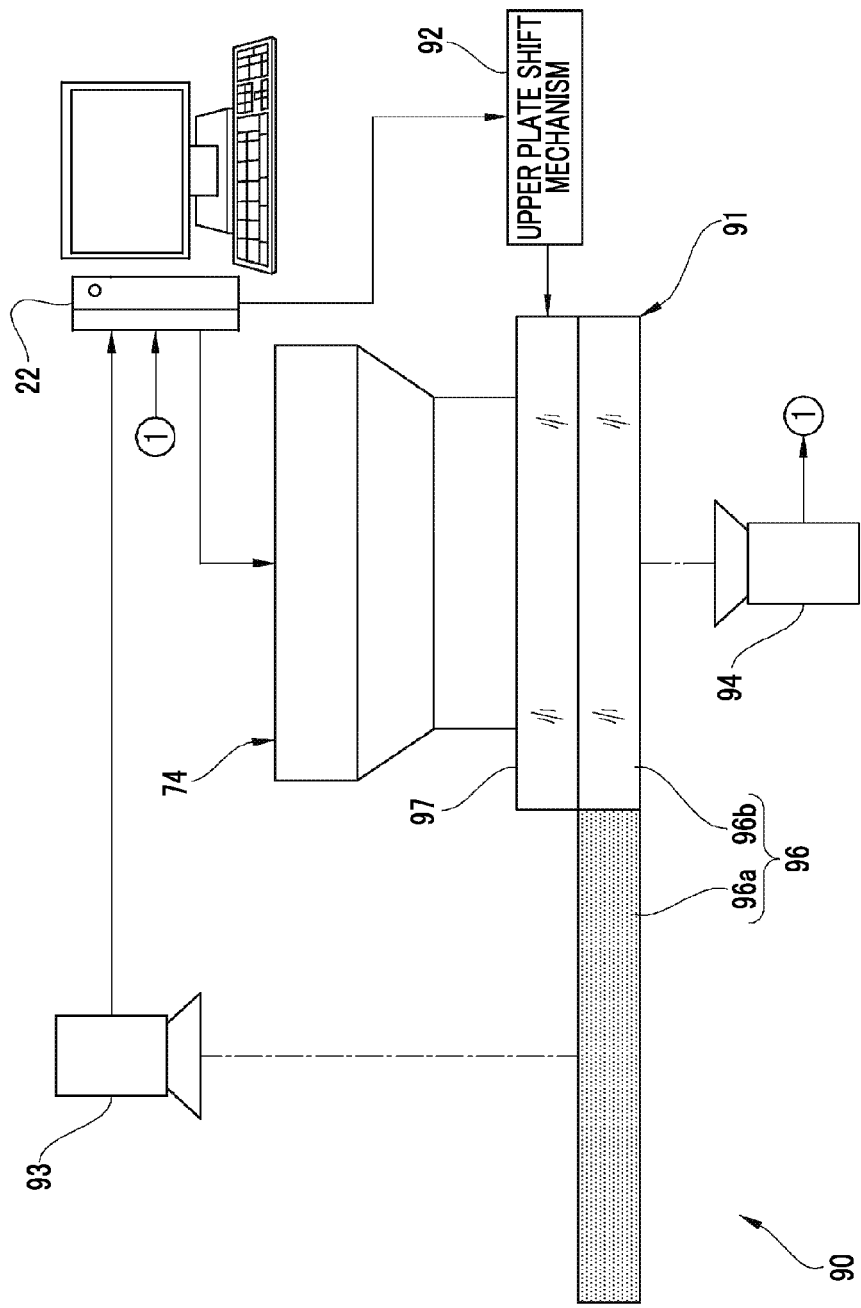
FIG. 19 is a diagram schematically illustrating the drug inspection device according to the fourth embodiment in which the upper plate is moved to a second position.

Next, a drug inspection device 90 according to a fourth embodiment of the invention will be described with reference to FIGS. 18 and 19. The drug inspection device according to each of the above-described embodiments captures the image of the drug 12 from the upper side. That is, the drug inspection device captures the image of the drug 12 from one side. However, the drug inspection device 90 captures the images of the drug 12 from both sides in the vertical direction.

The drug inspection device 90 has the same basic structure as the drug inspection device 70 according to the third embodiment except that it includes a switching stage (drug movement mechanism) 91 instead of the door 82 according to the third embodiment, an upper plate shift mechanism 92, a first camera (first imaging unit) 93, and a second camera (second imaging unit) 94. Therefore, components having the same functions and structures as those in the drug inspection device 70 (drug inspection device 10) according to the third embodiment are denoted by the same reference numerals and the description thereof will not be repeated.

The switching stage 91 includes a lower plate 96 and an upper transparent plate 97 which is provided on the lower plate 96 so as to be slidably in the horizontal direction. The lower plate 96 is formed by connecting a light shielding plate 96a and a transparent plate 96b.

The inspection pod 74 is set on the upper surface of the upper plate 97. The upper plate 97 is slid between a first position (see FIG. 18) on the light shielding plate 96a and a second position (see FIG. 19) on the transparent plate 96b by the upper plate shift mechanism 92. The upper plate shift mechanism 92 is driven to slide the upper plate 97 to the first position or the second position under the control of the overall control unit 30.

The first camera 93 is provided above the light shielding plate 96a. In a case in which the upper plate 97 is located at the first position, the first camera 93 captures the image of one surface of the drug 12, which is placed on the upper plate 97 in the inspection pod 74, through the upper opening portion 76a and generates captured image data 28 (hereinafter, referred to as first captured image data 28). Then, the first camera 93 outputs the first captured image data 28 to a device body 22 (see FIG. 18).

The second camera 94 is provided below the transparent plate 96b. In a case in which the upper plate 97 is located at the second position, the second camera 94 captures the image of the other surface that is opposite to the one surface of the drug 12, which is placed on the upper plate 97 in the inspection pod 74, through the transparent plate 96b and the upper plate 97 and generates captured image data 28 (hereinafter, referred to as second captured image data 28). Then, the second camera 94 outputs the second captured image data 28 to the device body 22 (see FIG. 19).

The device body 22 according to the fourth embodiment has the same basic structure as the device body 22 according to the first embodiment. However, each unit of the device body 22 according to the fourth embodiment separately processes the first and second captured image data items 28 acquired from the first camera 93 and the second camera 94.

A drug region extraction unit 37 according to the fourth embodiment extracts drug region image data 54 (hereinafter, referred to as first drug region image data 54) for each drug 12 from the first captured image data 28 in each illumination direction. In addition, the drug region extraction unit 37 extracts drug region image data 54 (hereinafter, referred to as second drug region image data 54) for each drug 12 from the second captured image data 28 in each illumination direction.

A feature image extraction unit 38 according to the fourth embodiment analyzes the first drug region image data 54 for each drug 12 in each illumination direction and extracts feature image data 58 (hereinafter, referred to as first feature image data 58) from each first drug region image data item 54. In addition, the feature image extraction unit 38 analyzes the second drug region image data 54 for each drug 12 in each illumination direction and extracts feature image data 58 (hereinafter, referred to as second feature image data 58) from each second drug region image data item 54.

A feature image integration unit 39 according to the fourth embodiment integrates the first feature image data 58 for each drug 12 in each illumination direction to generate integrated image data 60 (hereinafter, referred to as first integrated image data 60). In addition, the feature image integration unit 39 integrates the second feature image data 58 for each drug 12 in each illumination direction to generate integrated image data 60 (hereinafter, referred to as second integrated image data 60).

A drug recognition unit 43 according to the fourth embodiment recognizes the stamped character 14 included in each first integrated image data item 60 corresponding to one packet and recognizes the stamped character 14 included in each second integrated image data item 60 corresponding to one packet. Therefore, it is possible to individually recognize the stamped characters 14 on one surface and the other surface of each of the drugs 12 corresponding to one packet. Then, a drug recognition unit 43 according to the fourth embodiment recognizes the type of each drug corresponding to one packet, on the basis of the results of recognizing the stamped characters 14 on at least one of both surfaces of each drug 12.

An inspection unit 44, a display unit 45, and a storage unit 46 according to the fourth embodiment have the same structure as those in the first embodiment and thus the description thereof will not be repeated here.

After the drug recognition unit 43 recognizes the type of drug 12, the drug 12 is discharged from the inspection pod 74 into the drug passage by a drug discharge mechanism (not illustrated) and is then put from the hopper into the packet 11.

[Operation of Drug Inspection Device According to Fourth Embodiment]

Next, the operation of the drug inspection device 90 having the above-mentioned structure will be described with reference to FIG. 20. When an inspection start operation is performed through the operating unit 32 after the drugs 12 corresponding to one packet are put into the inspection pod 74 (Step S1A), the overall control unit 30 drives the upper plate shift mechanism 92 to set the upper plate 97 and the inspection pod 74 to the first position (Step S1B).

After the upper plate 97 and the inspection pod 74 are set to the first position, the overall control unit 30 operates each unit of the device body 22 and performs the process from Step S4 to Step S11 described in the first embodiment. Then, the first camera 93 captures an image whenever the illumination direction of the inspection pod 74 is switched. Then, the extraction of the first drug region image data 54, the extraction of the first feature image data 58, and the generation of the first integrated image data 60 are performed on the basis of the first captured image data 28 obtained by the imaging operation.

Then, the overall control unit 30 drives the upper plate shift mechanism 92 to set the upper plate 97 and the inspection pod 74 to the second position (Step S11A). Then, after the upper plate 97 and the inspection pod 74 are set to the second position, the overall control unit 30 operates each unit of the device body 22 and performs the process from Step S4-1 to Step S11-1 which is the same as the process from Step S4 to Step S11 (Steps S6-1 to S8-1 are not illustrated). In this case, the second camera 94 captures an image whenever the illumination direction of the inspection pod 74 is switched. Then, the extraction of the second drug region image data 54, the extraction of the second feature image data 58, and the generation of the second integrated image data 60 are performed on the basis of the second captured image data 28 obtained by the imaging operation.

After the second integrated image data 60 is generated, the drug recognition unit 43 recognizes the stamped character 14 on at least one of both surfaces of each drug 12 corresponding to one packet, on the basis of the first integrated image data 60 and the second integrated image data 60 corresponding to one packet. Then, the drug recognition unit 43 recognizes the type of each drug corresponding to one packet, on the basis of the results of recognizing the stamped characters 14 (Step S12).

Figure 20:
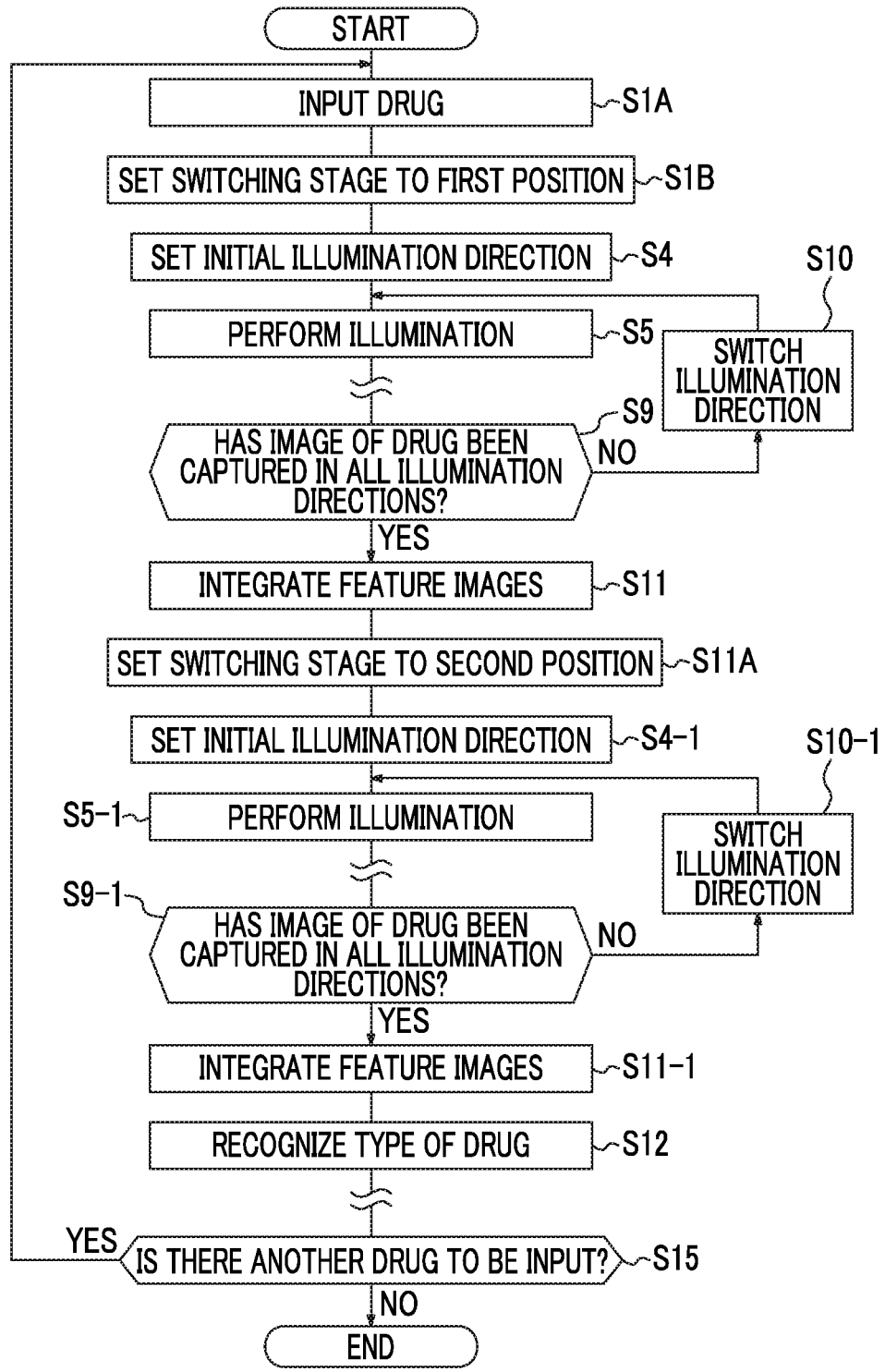
FIG. 20 is a flowchart illustrating the flow of an inspection process of the drug inspection device according to the fourth embodiment.

Then, the inspection unit 44 performs collation (inspection) and the collation result of the inspection unit 44 is displayed on the display unit 45 (Steps S13 and S14 are not illustrated in FIG. 20).

Then, each of the above-mentioned processes is repeatedly performed whenever the drugs 12 corresponding to one packet are put into the inspection pod 74 (Step S15).

[Operation and Effect of Drug Inspection Device According to Fourth Embodiment]

As such, the drug inspection device 90 according to the fourth embodiment captures the images of both surfaces of the drug 12. Therefore, even in a case in which the stamped character 14 is formed on only one of both surfaces of the drug 12, it is possible to recognize the stamped character 14 and to recognize the type of drug 12.

[Other Examples of Structure of Drug Inspection Device According to Fourth Embodiment]

In the fourth embodiment, the case in which the images of both surfaces of the drug 12 are captured in the third embodiment using the inspection pod 74 has been described. However, the images of both surfaces of the drug 12 may be captured in the first embodiment or the second embodiment using the floodlight 19 and in a combination of the second embodiment and the third embodiment. In addition, the following structure may be used, instead of shifting the upper plate 97 to move the inspection pod 74 to the first position and the second position: a transparent rotating stage is provided at the center of the lower plate 96; and the rotating stage is rotated to move the inspection pod 74 to the first position and the second position.

[Drug Inspection Device According to Fifth Embodiment]

Figure 21:
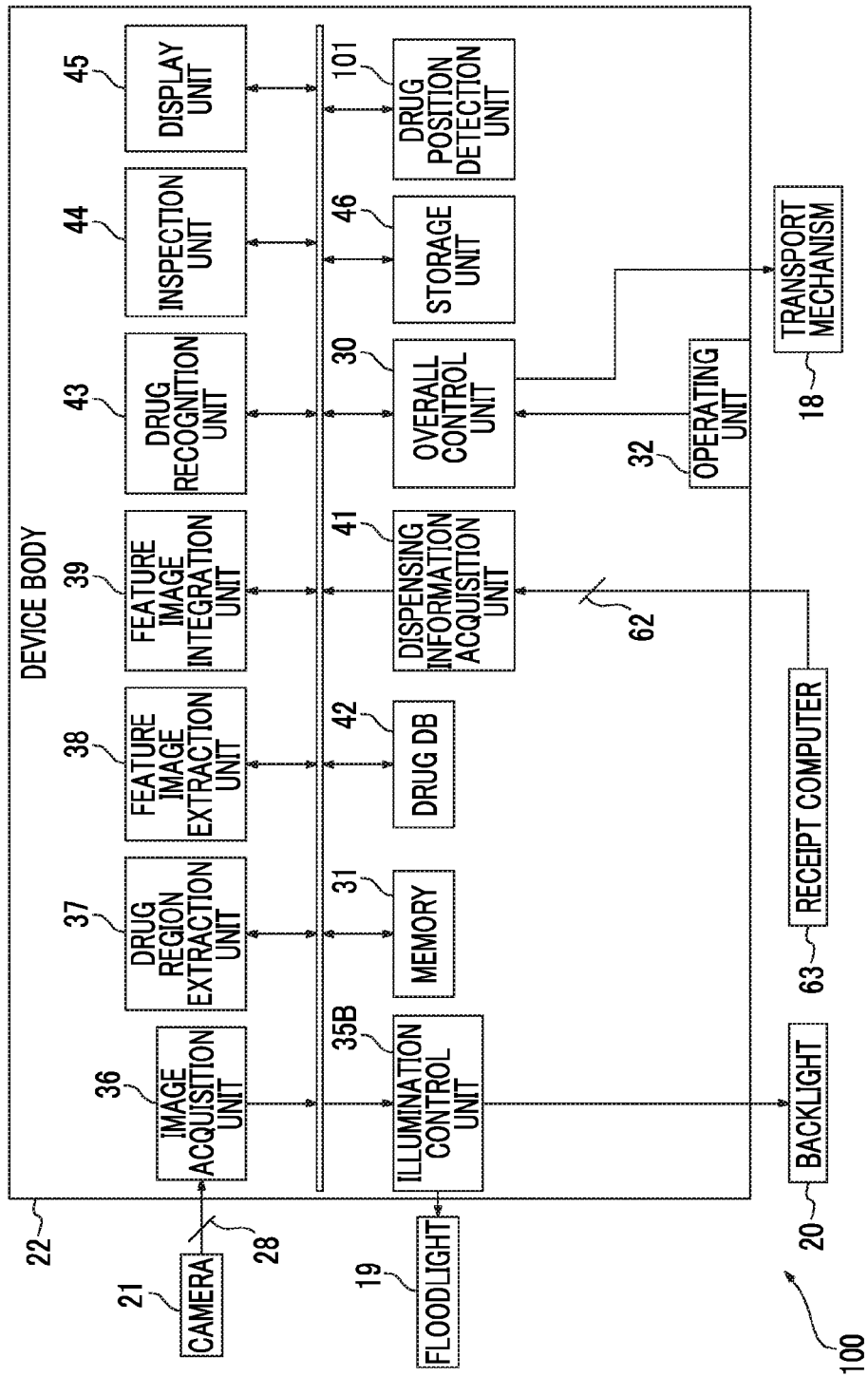
FIG. 21 is a block diagram illustrating the electrical structure of a drug inspection device according to a fifth embodiment.

Next, a drug inspection device 100 according to a fifth embodiment of the invention will be described with reference to FIG. 21. In the second embodiment, "high angle", "low angle", "backlight", "light amount adjustment", and "switching the illumination direction four times/eight times" are given as an example of the sub-illumination conditions. However, in the drug inspection device 100, the sub-illumination conditions further include "individual light amount adjustment".

Figure 22:
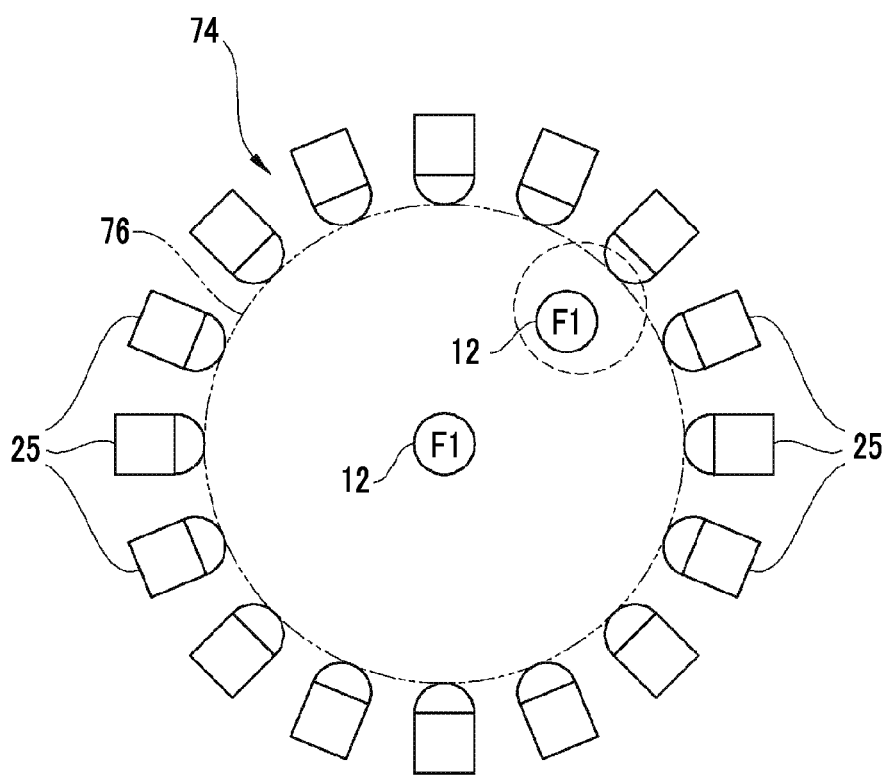
FIG. 22 is a diagram illustrating a process of calculating the positional relationship between a drug in an inspection pod and each point light source 25.

Under the sub-illumination condition "individual light amount adjustment", the amount of illumination light in each illumination direction is adjusted according to the position of the drug 12 in the light source holding unit 24. As illustrated in FIG. 22, the amount of illumination light which is incident on the drug 12 located in the vicinity of the center of the light source holding unit 24 from each point light source 25 is substantially uniform.

In contrast, for the drug 12 (the drug 12 surrounded by a dotted line in FIG. 22) which is located in the vicinity of the edge of the light source holding unit 24, since the distance between each point light source 25 and the drug 12 is not constant, the amount of illumination light which is incident on the drug 12 from each point light source 25 is not uniform. Therefore, a large amount of illumination light is incident on the drug 12 from the point light source 25 which is close to the drug 12 and a small amount of illumination light is incident on the drug 12 from the point light source 25 which is far away from the drug 12. Therefore, the brightness distribution of the drug 12 in the captured image data 28 is uneven. In particular, since a large amount of illumination light is incident on the drug 12 from the point light source 25 which is close to the drug 12, halation occurs in the drug 12 in the captured image data 28. As a result, there is a concern that the recognition of the stamped character 14 will fail.

For this reason, under the sub-illumination condition "individual light amount adjustment", the amount of illumination light in each illumination direction (that is, from each point light source 25) is individually adjusted according to the position of the drug 12 in the light source holding unit 24 such that the amount of illumination light which is incident on the drug 12 in each illumination direction is uniform.

Returning to FIG. 21, the drug inspection device 100 has the same basic structure as the drug inspection device 65 according to the second embodiment except that it includes a drug position detection unit 101 and an illumination control unit 35B which is different from the illumination control unit 35A according to the second embodiment. Therefore, components having the same functions and structures as those in the drug inspection device 65 according to the second embodiment (the drug inspection device 10 according to the first embodiment) are denoted by the same reference numerals and the description thereof will not be repeated.

The drug position detection unit 101 reads the captured image data 28 from the captured image memory 48 and analyzes the captured image data 28 to detect the position of each drug 12 included in the captured image data 28 (for example, the direction from the center of the light source holding unit 24 and a direction). For example, the drug position detection unit 101 extracts the contour of the drug 12 in the image, using a known edge detection process or a known segmentation process, to detect the position of each drug 12, similarly to the drug region extraction unit 37. In this case, the drug region extraction unit 37 may function as the drug position detection unit 101. The drug position detection unit 101 outputs the detection result of the position of the drug 12 to the illumination control unit 35B.

The illumination control unit 35B has the same basic structure as the illumination control unit 35A according to the second embodiment. However, the illumination control unit 35B can switch the sub-illumination condition to "individual light amount adjustment". The set content of "individual light amount adjustment" varies depending on the position of the drug 12 in the light source holding unit 24. Therefore, the illumination control unit 35B determines the set content of "individual light amount adjustment" in advance.

Figure 23:
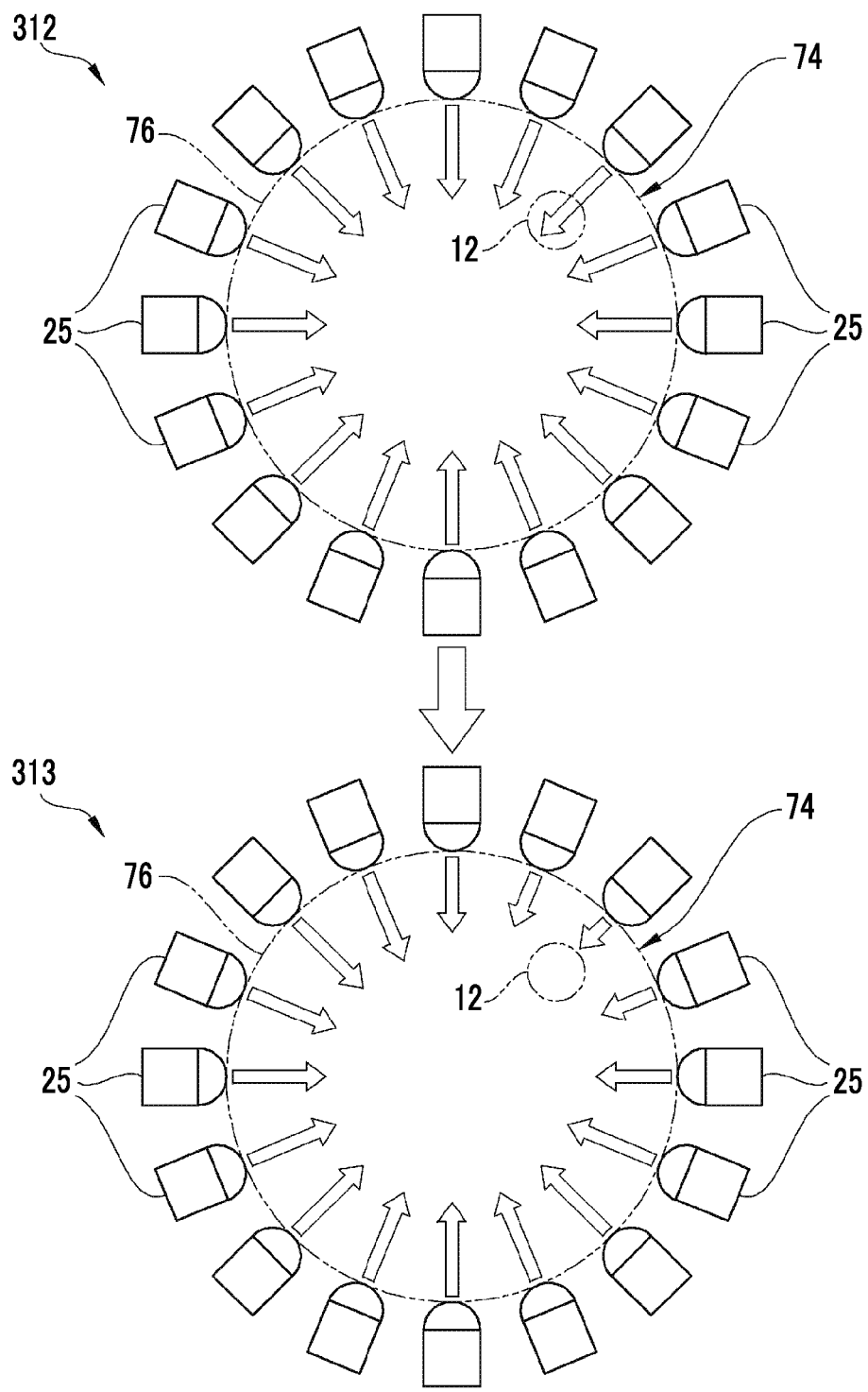
FIG. 23 is a diagram illustrating the individual adjustment of the amount of illumination light in each illumination direction by an illumination control unit.

As illustrated in FIG. 23, first, the illumination control unit 35B calculates the positional relationship between the each drug 12 in the light source holding unit 24 and each point light source 25, on the basis of the detection result of the position of the drug 12 which is input from the drug position detection unit 101 and the known size information of the light source holding unit 24 (see reference numeral 312). The "positional relationship" is, for example, the direction of each point light source 25 relative to the drug 12 and the distance between each point light source 25 and the drug 12.

Then, with respect to each drug 12 in the light source holding unit 24, the illumination control unit 35B determines, on the basis of the calculation result of the positional relationship, the amount of illumination light in each illumination direction (from each point light source 25) to uniformize the amount of illumination light incident on each drug 12 in each illumination direction, as the sub-illumination condition "individual light amount adjustment" (see reference numeral 313).

Figure 24:
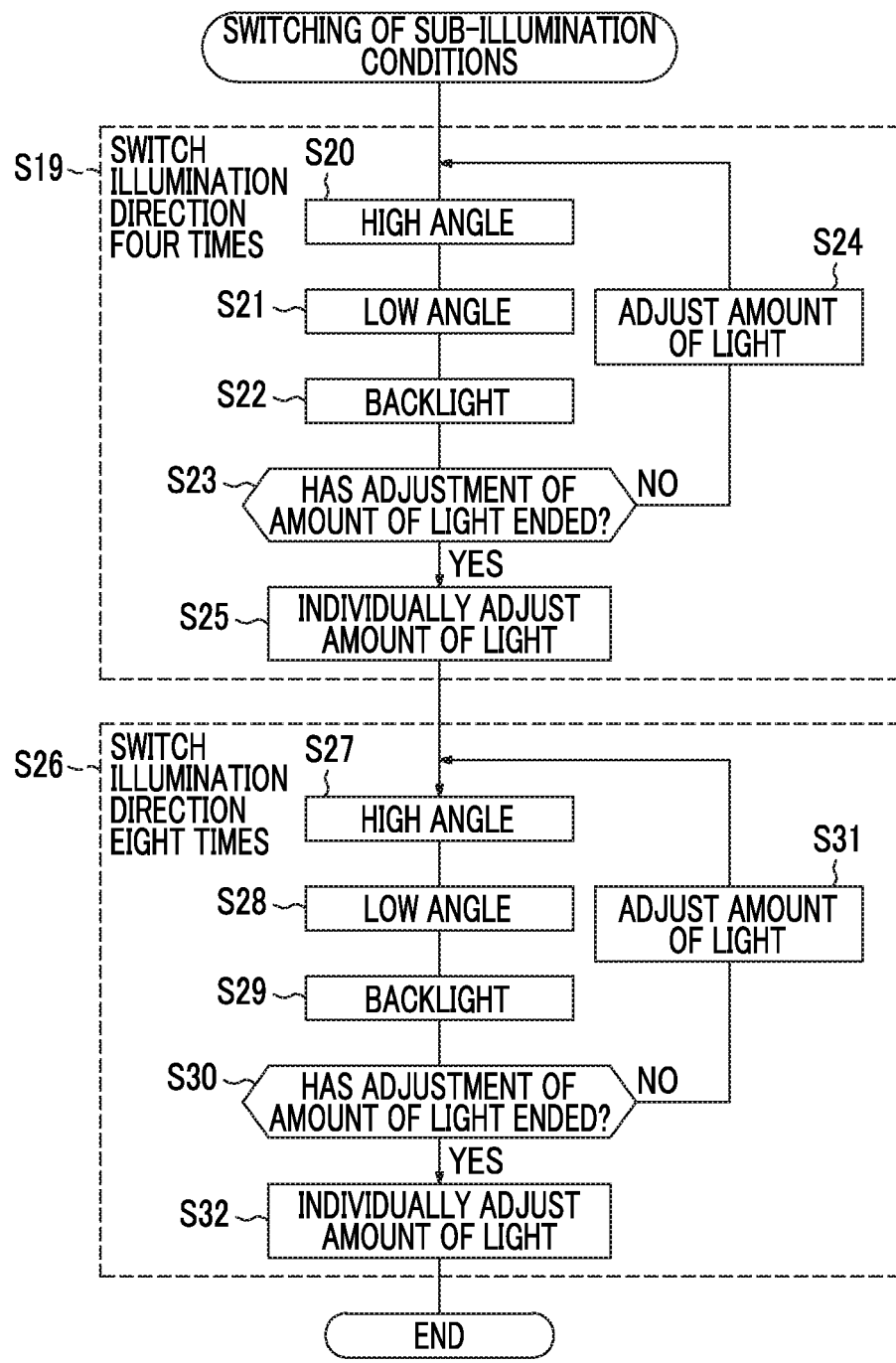
FIG. 24 is a flowchart illustrating the switching of sub-illumination conditions by the illumination control unit.

As illustrated in FIG. 24, when the sub-illumination condition described in the second embodiment is switched, the illumination control unit 35B can switch the sub-illumination condition to "individual light amount adjustment" (Steps S25 and S32). Then, in a case in which the sub-illumination condition is switched to "individual light amount adjustment", first, the illumination control unit 35B performs the process of switching the illumination direction four times/eight times according to the set content of "individual light amount adjustment" corresponding to a first drug 12 in the light source holding unit 24.

Then, the illumination control unit 35B performs the process of switching the illumination direction four times/eight times according to the set content of "individual light amount adjustment" corresponding to a second drug 12 in the light source holding unit 24. Similarly, the illumination control unit 35B repeatedly performs the process of switching the illumination direction four times/eight times according to the set content of "individual light amount adjustment" corresponding to each drug 12 in the light source holding unit 24.

At that time, the drug 12 (masked drug 12), of which the type has been successfully recognized, may be excluded from the drugs to be subjected to "individual light amount adjustment". In addition, the drug 12 which is located in the vicinity of the center of the light source holding unit 24 on the basis of the detection result of the position of the drug 12 may be excluded from the drugs to be subjected to "individual light amount adjustment". In this case, it is possible to reduce the time required to recognize the drug 12.

[Operation and Effect of Drug Inspection Device According to Fifth Embodiment]

As described above, in the drug inspection device 100 according to the fifth embodiment of the invention, when the illumination direction is switched, a uniform amount of illumination light can be incident on the drug 12 in each illumination direction. Therefore, it is possible to uniformize the brightness distribution of the drug 12 in the captured image data 28. As a result, the occurrence of halation in the captured image of the drug 12 which is located in the vicinity of the edge of the light source holding unit 24 is prevented and the probability of success in recognizing the types of drug 12 (stamped character 14) which is located in the vicinity of the edge of the light source holding unit 24 increases.

The structure according to the fifth embodiment can be applied to the case in which the drug 12 is illuminated by the inspection pod 74 as described in the third embodiment.

[Drug Inspection Device According to Sixth Embodiment]

Figure 25:
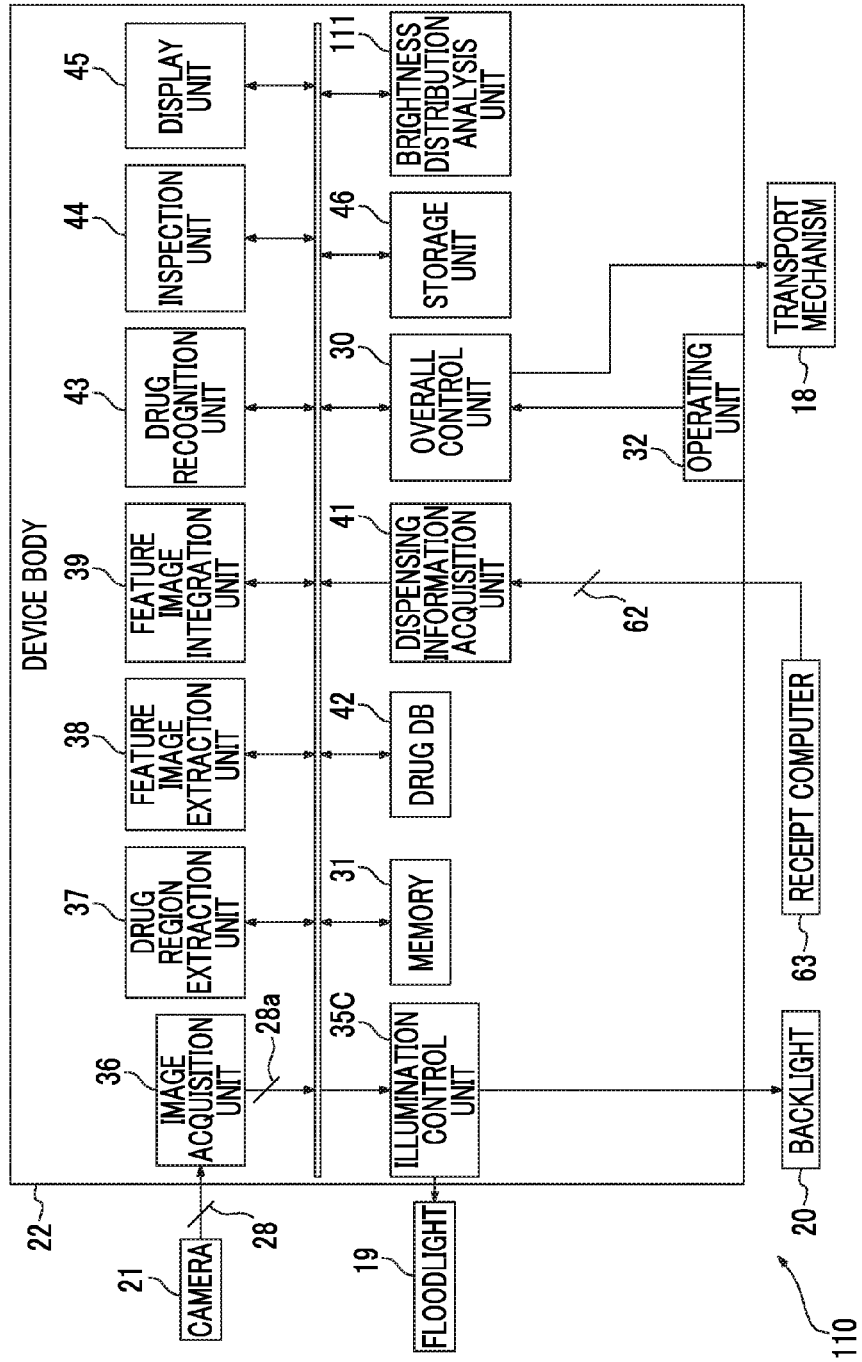
FIG. 25 is a block diagram illustrating the electrical structure of a drug inspection device according to a sixth embodiment.

Next, a drug inspection device 110 according to a sixth embodiment of the invention will be described with reference to FIG. 25. The drug inspection device 100 according to the fifth embodiment switches the sub-illumination condition to "individual light amount adjustment" to individually adjust the amount of illumination light in each illumination direction according to the position of the drug 12 in the light source holding unit 24. In contrast, in a case in which the sub-illumination condition is switched to "individual light amount adjustment", the drug inspection device 110 individually adjusts the amount of illumination light in each illumination direction on the basis of the brightness distribution of the image of the drug 12.

The drug inspection device 110 has the same basic structure as the drug inspection device 100 according to the fifth embodiment except that it includes a brightness distribution analysis unit 111 and an illumination control unit 35C, instead of the drug position detection unit 101 and the illumination control unit 35B. Therefore, components having the same functions and structures as those in the drug inspection device 100 according to the fifth embodiment (for example, the drug inspection device 10 according to the first embodiment) are denoted by the same reference numerals and the description thereof will not be repeated.

An overall control unit 30 according to the sixth embodiment controls the illumination control unit 35C in advance such that the floodlight 19 illuminates the drug 12 in all of the illumination directions at the same time before the illumination direction of the floodlight 19 is switched. Then, the overall control unit 30 controls the image acquisition unit 36 such that the camera 21 captures the image of the drug 12 which is illuminated by the floodlight 19 in all of the illumination directions at the same time. Then, the image acquisition unit 36 acquires previously captured image data 28a from the camera 21 and stores the previously captured image data 28a in the captured image memory 48.

Figure 26:
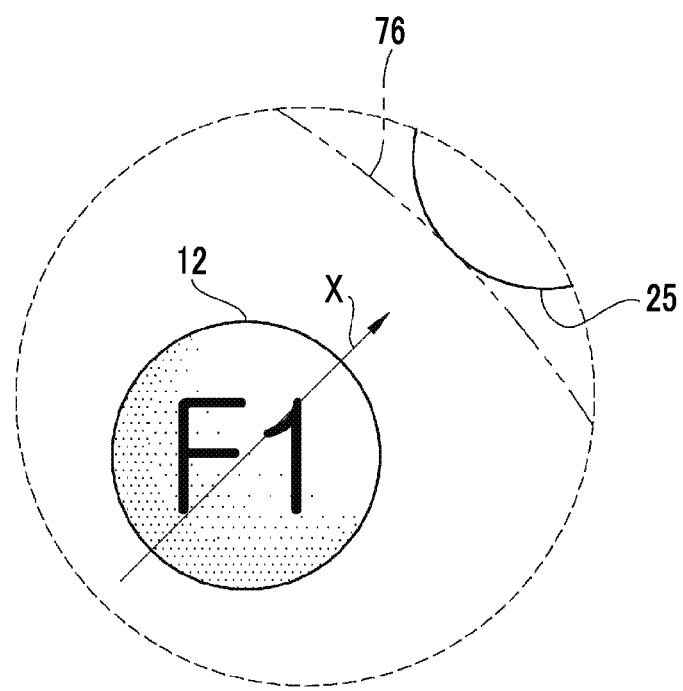
FIG. 26 is a diagram illustrating the brightness distribution of the image of a drug and the direction of a brightness gradient.

In FIG. 26 which is an enlarged view illustrating a dotted circle in FIG. 22, the brightness distribution analysis unit 111 reads the previously captured image data 28a from the captured image memory 48, detects the position of each drug 12 in the image, similarly to the drug region extraction unit 37, and analyzes the brightness distribution of the image of each drug 12. Then, the brightness distribution analysis unit 111 outputs the analysis result of the brightness distribution of each drug 12 to the illumination control unit 35C.

The illumination control unit 35C has the same basic structure as the illumination control unit 35B according to the fifth embodiment and determines the content of "individual light amount adjustment" set for each drug 12, on the basis of the analysis result of the brightness distribution of each drug 12 which is input from the brightness distribution analysis unit 111. First, the illumination control unit 35C calculates the direction X (the direction in which the brightness is the highest) of a brightness gradient for each drug 12, on the basis of the analysis result of the brightness distribution of each drug 12.

Then, with respect to each drug 12, the illumination control unit 35C determines the amount of illumination light in each illumination direction to uniformize the amount of illumination light incident on each drug 12 in each illumination direction, on the basis of the calculation result of the direction X of the brightness gradient for each drug 12. In this way, the set content of the sub-illumination condition "individual light amount adjustment" is determined.

Then, similarly to the fifth embodiment, in a case in which the sub-illumination condition is switched to "individual light amount adjustment", the illumination control unit 35C repeatedly performs the process of switching the illumination direction four times/eight times, according to the content of "individual light amount adjustment" set for each drug 12 in the light source holding unit 24. In this way, the same effect as that described in the fifth embodiment is obtained.

The structure according to the sixth embodiment can be applied to the case in which the drug 12 is illuminated by the inspection pod 74 as described in the third embodiment.

[Others]

In each of the above-described embodiments, the number of times the illumination direction is switched is set to 4 or 8. However, the number of times the illumination direction is switched can change to any value.

For example, in the second embodiment, for example, "high angle". "low angle", "backlight", "light amount adjustment", and "switching the illumination direction four times/eight times" are given as an example of the sub-illumination conditions. However, for example, the sub-illumination conditions may include the color of illumination light or the type of illumination light (parallel light or diffused light).

In each of the above-described embodiments, the drug 12 is illuminated in a plurality of illumination directions by the floodlight 19 or the inspection pod 74. However, various types of illumination units which can illuminate the drug 12 in a plurality of illumination directions that surround the drug 12 may be used.

In each of the above-described embodiments, the drug recognition device according to the invention is applied to the drug inspection device. However, the invention can be applied various devices which can recognize the type of drug 12 having the stamped character 14 thereon.

EXPLANATION OF REFERENCES 10, 65, 70, 90, 100, 110: drug inspection device
11: packet
12: drug
19: floodlight
21: camera
25: point light source
35, 35A. 35B, 35C: illumination control unit
37: drug region extraction unit
38: feature image extraction unit
39: feature image integration unit
43: drug recognition unit
44: inspection unit
67: masking unit
74: inspection pod
93: first camera
94: second camera
101: drug position detection unit
111: brightness distribution analysis unit

What is claimed is:

1. A drug recognition device comprising:
a light the illuminates a drug having a stamped character thereon, said light illuminating the drug in a plurality of illumination directions;
a camera that captures images of the drug illuminated by the light; and
a processor programmed to perform operations of:
switching the illumination direction in which the light illuminates the drug;
controlling the camera to repeatedly capture at least one image of the drug whenever the illumination direction of the light is switched;
extracting a feature image corresponding to a shadow of the stamped character from the captured image of the drug in each illumination direction which is acquired by the camera;
integrating the feature images in each illumination direction which are extracted to generate an integrated image; and
recognizing the stamped character included in the integrated image and recognizing the type of the drug on the basis of the result of recognizing the stamped character,
wherein the light includes a first light source and a second light source, the first light source causes illumination light to be incident on the drug at a first incident angle in the illumination directions surrounding the drug, and the second light source causes illumination light to be incident on the drug at a second incident angle, is the second incident angle being different from the first incident angle, and
wherein the switching of the illumination direction of the light comprises: switching the first light source in a state in which the second light source is turned off, and switching of the illumination direction of the second light source in a state in which the first light source is turned off.

2. The drug recognition device according to claim 1, the processor is further programmed to perform operations of:
detecting the position of the image of the drug included in the captured image as a drug position,
wherein the light can change an amount of illumination light for illuminating the drug in each illumination direction, and
the processor is further programmed to perform calculating a positional relationship between the drug and the first light source and the second light source in each illumination direction, on the basis of the detection result of the drug position, and controls the light on the basis of the calculation result of the positional relationship such that a uniform amount of illumination light is incident on the drug in each illumination direction.

3. The drug recognition device according to claim 1,
wherein the light can change the amount of illumination light for illuminating the drug in each illumination direction,
the camera captures the image of the drug which is illuminated in all of the illumination directions at the same time by the light and wherein the processor is programmed to acquire a previously captured image,
the processor is further programmed to perform operation of analyzing a brightness distribution of the image of the drug included in the previously captured image, and controlling the light on the basis of the analysis result of the brightness distribution such that a uniform amount of illumination light is incident on the drug in each illumination direction.

4. The drug recognition device according to claim 1,
wherein the light can perform switching of sub-illumination conditions of the light which is different from the switching of the illumination direction and which includes at least switching of the first incident angle and the second incident angle, and
the processor is further programmed to perform controlling the light such that the illumination direction is switched under each sub-illumination condition, while switching the sub-illumination conditions.

5. The drug recognition device according to claim 4,
wherein the processor is further programmed to determine whether a plurality of drugs is included in the captured image, and in a case in which a plurality of drugs is included in the captured image, the processor controls the light such that the sub-illumination conditions are repeatedly switched until the recognition unit succeeds in recognizing the types of all of the drugs in the captured image.

6. The drug recognition device according to claim 5,
wherein the processor is programmed to stop the extraction of the feature image from a region corresponding to the drug, of which the type has been successfully recognized by the recognition unit, in the captured image.

7. The drug recognition device according to claim 1,
wherein the processor is further programmed to perform operations of:
acquiring dispensing information,
wherein the light illuminates each packet of drugs which are packaged in a plurality of packets according to the dispensing information, and
discriminating the stamped character on the drug which is recorded in the dispensing information acquired by the dispensing information acquisition, comparing the discrimination result of the stamped character with the integrated image to recognize the stamped character included in the integrated image, and recognizing the types of the drugs corresponding to one packet on the basis of the result of recognizing the stamped character.

8. The drug recognition device according to claim 7, wherein the processor is further programmed to perform operations of:
- collating the result of recognizing the types of the drugs corresponding to one packet with the types of the drugs corresponding to one packet which are recorded in the dispensing information; the drug recognition device further including a
- a display that displays the collation result.

9. The drug recognition device according to claim 1, wherein extracting the feature image comprises an edge detection process.

10. The drug recognition device according to claim 1,
- wherein the light includes a plurality of point light sources that are provided around the drugs, and
- switching the illumination direction comprises turning each of the point light sources on and off to switch the illumination direction.

11. The drug recognition device according to claim 1, further comprising:
- a drug movement mechanism that moves the drug and the light between a first position and a second position in a horizontal direction,
- wherein the camera includes a first camera that captures an image of one surface of the drug in a case in which the drug is at the first position and a second camera that captures an image of the other surface opposite to the one surface of the drug in a case in which the drug is at the second position,
- wherein extracting the feature image comprises extracting the feature images from the captured images in each illumination direction which are acquired by the first camera and the second camera,
- wherein integrating the feature images in each illumination direction includes integrating feature images which correspond to the one surface and integrating the feature images in each illumination direction which correspond to the other surface to generate the integrated images corresponding to the one surface and the other surface, and
- recognizing the stamped character includes recognizing the stamped character on at least one of the one surface and the other surface of the drug, on the basis of the integrated images corresponding to the one surface and the other surface, and recognizing the type of the drug.

12. A drug recognition method comprising:
- an illumination control step of sequentially switching a plurality of illumination directions which surround a drug having a stamped character thereon and in which an illumination unit can illuminate the drug;
- an imaging step of repeatedly capturing an image of the drug illuminated by the illumination unit whenever the illumination direction is switched in the illumination control step;
- a feature image extraction step of extracting a feature image corresponding to a shadow of the stamped character from the captured image in each illumination direction which is acquired in the imaging step;
- a feature image integration step of integrating the feature images in each illumination direction which are extracted in the feature image extraction step to generate an integrated image; and
- a recognition step of recognizing the stamped character on the basis of the integrated image generated in the feature image integration step and recognizing the type of the drug on the basis of the result of recognizing the stamped character,
- wherein the illumination unit includes a first illumination unit and a second illumination unit, the first illumination unit causes illumination light to be incident on the drug at a first incident angle in the illumination directions surrounding the drug, and the second illumination unit causes illumination light to be incident on the drug at a second incident angle, which is different from the first incident angle, in the illumination directions surrounding the drug, and
- the illumination control step includes a step of performing switching of the illumination direction of the first illumination unit in a state in which the second illumination unit is turned off, and a step of performing switching of the illumination direction of the second illumination unit in a state in which the first illumination unit is turned off.

13. The drug recognition method according to claim 12, further comprising:
- a drug position detection step of detecting the position of the image of the drug included in the captured image,
- wherein the illumination unit can change the amount of illumination light for illuminating the drug in each illumination direction, and
- the illumination control step includes a step of calculating a positional relationship between the drug and a light source in each illumination direction of the illumination unit, on the basis of the detection result of the drug position detection step, and controlling the illumination unit on the basis of the calculation result of the positional relationship such that a uniform amount of illumination light is incident on the drug in each illumination direction.

14. The drug recognition method according to claim 12,
- wherein the illumination unit can change the amount of illumination light for illuminating the drug in each illumination direction,
- the imaging step includes a step of capturing the image of the drug which is illuminated in all of the illumination directions at the same time by the illumination unit and acquiring a previously captured image,
- the drug recognition method further comprises a brightness distribution analysis step of analyzing a brightness distribution of the image of the drug included in the previously captured image, and
- the illumination control step includes a step of controlling the illumination unit on the basis of the analysis result of the brightness distribution analysis step such that a uniform amount of illumination light is incident on the drug in each illumination direction.

15. The drug recognition method according to claim 12,
- wherein the illumination unit can perform switching of sub-illumination conditions of the illumination unit which is different from the switching of the illumination direction and which includes at least switching of the first incident angle and the second incident angle, and
- the illumination control step includes a step of controlling the illumination unit such that the illumination direction is switched under each sub-illumination condition, while switching the sub-illumination conditions.

16. The drug recognition method according to claim 15,
- wherein, in a case in which an image of a plurality of drugs is included in the captured image, the illumination control step includes a step of controlling the illumination unit such that the sub-illumination conditions are repeatedly switched until the recognition step succeeds in recognizing the types of all of the drugs.

17. The drug recognition method according to claim 16, wherein the feature image extraction step includes a step of stopping the extraction of the feature image from a region corresponding to the drug, of which the type has been successfully recognized in the recognition step, in the captured image.

18. The drug recognition method according to claim 12, further comprising:
a dispensing information acquisition step of acquiring dispensing information,
wherein the illumination step includes a step of illuminating each packet of drugs which are packaged in a plurality of packets according to the dispensing information, and
the recognition step includes a step of discriminating the stamped character on the drug which is recorded in the dispensing information acquired in the dispensing information acquisition step, comparing the discrimination result of the stamped character with the integrated image to recognize the stamped character included in the integrated image, and recognizing the types of the drugs corresponding to one packet on the basis of the result of recognizing the stamped character.

19. The drug recognition method according to claim 18, further comprising:
an inspection step of collating the result of recognizing the types of the drugs corresponding to one packet obtained in the recognition step with the types of the drugs corresponding to one packet which are recorded in the dispensing information; and
a display step of displaying the collation result of the inspection unit.

20. The drug recognition method according to claim 12, further comprising:
a drug movement step of moving the drug and the illumination unit between a first position and a second position in a horizontal direction,
wherein the imaging step includes a first imaging step of capturing an image of one surface of the drug in a case in which the drug is at the first position and a second imaging step of capturing an image of the other surface opposite to the one surface of the drug in a case in which the drug is at the second position,
the feature image extraction step includes a step of extracting the feature images from the captured images in each illumination direction which are acquired in the first imaging step and the second imaging step,
the feature image integration step includes a step of integrating the feature images in each illumination direction which correspond to the one surface and integrating the feature images in each illumination direction which correspond to the other surface to generate the integrated images corresponding to the one surface and the other surface, and
the recognition step includes a step of recognizing the stamped character on at least one of the one surface and the other surface of the drug, on the basis of the integrated images corresponding to the one surface and the other surface, and recognizing the type of the drug.

* * * * *